US012612644B2

(12) United States Patent
Gillmeister et al.

(10) Patent No.: US 12,612,644 B2
(45) Date of Patent: Apr. 28, 2026

(54) SCALABLE METHOD FOR RECOMBINANT AAV PRODUCTION

(71) Applicant: REGENXBIO Inc., Rockville, MD (US)

(72) Inventors: Michael Gillmeister, Hanover, MD (US); Miguel Valle, Potomac, MD (US); Robert Stadelman, New Market, MD (US); Franz Gerner, Myersville, MD (US); Matthieu Guibert, Germantown, MD (US); Bhargavi Kondragunta, Clarksburg, MD (US)

(73) Assignee: REGENXBIO INC., Rockville, MD (US)

( * ) Notice: Subject to any disclaimer, the term of this patent is extended or adjusted under 35 U.S.C. 154(b) by 929 days.

(21) Appl. No.: 17/267,247

(22) PCT Filed: Aug. 9, 2019

(86) PCT No.: PCT/US2019/045926
§ 371 (c)(1),
(2) Date: Feb. 9, 2021

(87) PCT Pub. No.: WO2020/033842
PCT Pub. Date: Feb. 13, 2020

(65) Prior Publication Data
US 2021/0163991 A1     Jun. 3, 2021

Related U.S. Application Data

(60) Provisional application No. 62/717,212, filed on Aug. 10, 2018.

(51) Int. Cl.
| | |
|---|---|
| *C12N 15/86* | (2006.01) |
| *C07K 14/01* | (2006.01) |
| *C07K 14/015* | (2006.01) |
| *C12N 15/85* | (2006.01) |
| *C12N 15/864* | (2006.01) |

(52) U.S. Cl.
CPC .............. *C12N 15/86* (2013.01); *C07K 14/01* (2013.01); *C07K 14/015* (2013.01); *C12N 15/85* (2013.01); *C12N 15/8645* (2013.01); *C12N 2750/14151* (2013.01); *C12N 2750/14152* (2013.01)

(58) Field of Classification Search
CPC .......... C12N 15/86; C12N 2750/14152; C12N 2750/14151; C12N 7/00; C12N 15/85; C07K 14/01
USPC ............ 435/320.1; 91.4; 536/23.72; 530/826
See application file for complete search history.

(56) References Cited

U.S. PATENT DOCUMENTS

| | | | |
|---|---|---|---|
| 6,413,776 B1 | 7/2002 | Vogels | |
| 6,566,118 B1 * | 5/2003 | Atkinson ............. | C07D 207/32 435/235.1 |
| 6,596,535 B1 | 7/2003 | Carter et al. | |
| 6,723,551 B2 | 4/2004 | Kotin et al. | |
| 6,995,006 B2 | 2/2006 | Atkinson et al. | |
| 7,125,717 B2 | 10/2006 | Carter et al. | |
| 7,282,199 B2 | 10/2007 | Gao et al. | |
| 7,456,683 B2 | 11/2008 | Takano et al. | |
| 7,906,111 B2 | 3/2011 | Wilson et al. | |
| 8,524,446 B2 | 9/2013 | Gao et al. | |
| 8,628,966 B2 | 1/2014 | Chatterjee et al. | |
| 8,734,809 B2 | 5/2014 | Gao et al. | |
| 8,927,514 B2 | 1/2015 | Chatterjee et al. | |
| 8,999,678 B2 | 4/2015 | Vandenberghe et al. | |
| 9,169,299 B2 | 10/2015 | Lisowski et al. | |
| 9,193,956 B2 | 11/2015 | Schaffer et al. | |
| 9,284,357 B2 | 3/2016 | Gao et al. | |
| 9,409,953 B2 | 8/2016 | Asokan et al. | |
| 9,458,517 B2 | 10/2016 | Schaffer et al. | |
| 9,585,971 B2 | 3/2017 | Deverman et al. | |
| 9,587,282 B2 | 3/2017 | Schaffer et al. | |
| 9,783,826 B2 | 10/2017 | Knop et al. | |
| 9,840,719 B2 | 12/2017 | High et al. | |
| 9,923,120 B2 | 3/2018 | Minato | |
| 2005/0080027 A1 | 4/2005 | Horer et al. | |

(Continued)

FOREIGN PATENT DOCUMENTS

| | | |
|---|---|---|
| EP | 3039129 | 7/2016 |
| WO | 03/042397 | 5/2003 |

(Continued)

OTHER PUBLICATIONS

Adamson-Small L, Potter M, Byrne BJ, Clã © ment N. Sodium Chloride Enhances Recombinant Adeno-Associated Virus Production in a Serum-Free Suspension Manufacturing Platform Using the Herpes Simplex Virus System. Hum Gene Ther Methods. Feb. 2017; 28(1):1-14. (Year: 2017).*

(Continued)

*Primary Examiner* — Anne Marie S Wehbe
*Assistant Examiner* — Katie L Pennington
(74) *Attorney, Agent, or Firm* — Nixon & Vanderhye PC

(57) ABSTRACT

Provided herein are improved methods for producing recombinant Adeno-Associated Virus (rAAV) particles. In some embodiments, a method for producing recombinant AAV (rAAV) particles provided herein comprises culturing cells capable of producing rAAV particles in the presence of a histone deacetylase (HDAC) inhibitor. In some embodiments, a method for producing recombinant AAV (rAAV) particles provided herein comprises culturing cells capable of producing rAAV particles in the presence of a histone deacetylase (HDAC) inhibitor and increased amount of a sodium salt.

14 Claims, 5 Drawing Sheets

(56) References Cited

U.S. PATENT DOCUMENTS

| | | |
|---|---|---|
| 2009/0069266 A1 | 3/2009 | Dean |
| 2009/0275107 A1 | 11/2009 | Lock et al. |
| 2011/0212526 A1 | 9/2011 | Hu et al. |
| 2012/0122155 A9 | 5/2012 | Balloul et al. |
| 2013/0224836 A1 | 8/2013 | Muramatsu |
| 2013/0316400 A1 | 11/2013 | Vasu |
| 2014/0242671 A1 | 8/2014 | Grieger et al. |
| 2015/0023924 A1 | 1/2015 | High et al. |
| 2015/0126588 A1 | 5/2015 | Nakai et al. |
| 2015/0211021 A1 | 7/2015 | De Mollerat Du Jeu |
| 2015/0374803 A1 | 12/2015 | Wolfe |
| 2016/0215024 A1 | 7/2016 | Vandenberghe et al. |
| 2016/0222356 A1 | 8/2016 | Zhao et al. |
| 2016/0376323 A1 | 12/2016 | Schaffer et al. |
| 2017/0016043 A1 | 1/2017 | Zmuda |
| 2017/0051257 A1 | 2/2017 | Vandenberghe et al. |
| 2017/0067908 A1 | 3/2017 | Nakai et al. |
| 2017/0362577 A1 | 12/2017 | Hwang et al. |
| 2018/0135077 A1 | 5/2018 | Yu |
| 2018/0143117 A1 | 5/2018 | He |
| 2020/0224173 A1* | 7/2020 | Clement ................. C12N 7/00 |

FOREIGN PATENT DOCUMENTS

| | | | | |
|---|---|---|---|---|
| WO | 2003/052051 | 6/2003 | | |
| WO | 2005/033321 | 4/2005 | | |
| WO | 2006/068888 | 6/2006 | | |
| WO | 2006/110689 | 10/2006 | | |
| WO | 2009/104964 | 8/2009 | | |
| WO | 2010/127097 | 11/2010 | | |
| WO | 2013/166339 A1 | 11/2013 | | |
| WO | 2014/172669 | 10/2014 | | |
| WO | 2015/013313 A2 | 1/2015 | | |
| WO | 2015/031686 | 3/2015 | | |
| WO | 2015031686 A1 | 3/2015 | | |
| WO | 2015089487 A1 | 6/2015 | | |
| WO | 2015/121501 | 8/2015 | | |
| WO | 2016/049230 | 3/2016 | | |
| WO | 2015/191508 | 12/2016 | | |
| WO | 2017/042337 | 3/2017 | | |
| WO | 2017/070491 | 4/2017 | | |
| WO | 2017/112948 | 6/2017 | | |
| WO | 2017151733 A1 | 9/2017 | | |
| WO | 2017201258 A1 | 11/2017 | | |
| WO | 2017214378 A1 | 12/2017 | | |
| WO | 2018/175775 | 9/2018 | | |
| WO | 2018/226887 | 12/2018 | | |
| WO | WO-2018226887 A1 * | 12/2018 | ............ | C12N 15/09 |
| WO | 2019/212921 | 11/2019 | | |
| WO | 2019/241535 | 12/2019 | | |

OTHER PUBLICATIONS

Thermo-Fisher Scientific, Dulbeccoâs Modified Eagle Medium (D-MEM), (1X) liquid (high glucose), [retrieved on Jan. 11, 2024], retrieved from the Internet: <URL: https://www.thermofisher.com/us/en/home/technical-resources/media-formulation.183.html>. (Year: 2024).*

Waldecker M, Kautenburger T, Daumann H, Busch C, Schrenk D. Inhibition of histone-deacetylase activity by short-chain fatty acids and some polyphenol metabolites formed in the colon. J Nutr Biochem. Sep. 2008; 19(9):587-93. Epub Dec. 3, 2007. (Year: 2007).*

Adamson-Small et al., "Sodium Chloride Enhances Recombinant Adeno-Associated Virus Production in a Serum-Free Suspension Manufacturing Platform Using the Herpes Simplex Virus System," Human Gene Therapy Methods, vol. 28, No. 1, pp. 1-14 (2017).

Backliwal et al., "Valproic Acid: A Viable Alternative to Sodium Butyrate for Enhancing Protein Expression in Mammalian Cell Cultures," Biotechnology and Bioengineering, vol. 101, No. 1, pp. 182-189 (2008).

Cervera et al., "Selection and optimization of transfection enhancer additives for increased virus-like particle production in HEK293 suspension cell cultures," Appl. Microbiol Biotechnol; 99; pp. 9935-9949 (2015).

Chun et al., "Enhanged production of recombinant B-domain deleted factor VII from Chinese hamster ovary cells by propionic and butyric acids," Biotechnology Letters, 25; pp. 315-319 (2003).

Cribbs et al., "Simplified production and concentration of lentiviral vectors to achieve high transduction in primary human T cells," BMC Biotechnology, 13:98, pp. 1-8 (2013).

Eckschlager et al., "Histone Deacetylase Inhibitors as Anticancer Drugs," International Journal of Molecular Sciences, 18:1414; pp. 1-25 (2017).

Fike, Richard, Nutrient Supplementation Strategies for Biopharmaceutical Production, Part 2, BioProcess International, 6 pgs. (2009).

Huber et al., "Inhibitors of Histone Deacetylases, Correlation Between Isoform specificity and reactivation of HIV type 1 (HIV-1) from latently infected cells," The Journal of Biological Chemistry, vol. 286, No. 25, pp. 22211-22218 (2011).

Jager et al., "Transient Recombinant Protein Expression in Mammalian Cells," Animal Cell Culture, pp. 27-64 (2015).

Kim et al., "Combinatorial Treatment with Lithium Chloride Enhances Recombinant Antibody Production in Transiently Transfected CHO and HEK293E Cells," Biotechnology and Bioprocess Engineering, 21: pp. 667-675 (2016).

Leng et al., "Valproic Acid and Other HDAC Inhibitors Upregulate FGF21 Gene Expression and Promote Process Elongation in Glia by Inhibiting HDAC2 and 3," International Journal of Neuropsychopharmacology, 19(8); pp. 1-13 (2016).

Steliou et al., "Butyrate Histone Deacetylase Inhibitors," BioResearch Open Access, vol. 1, No. 4, pp. 192-198 (2012).

Vazquez-Lombardi et al., "Transient expression of human antibodies in mammalian cells," Nature Protocols, vol. 13, No. 1, pp. 99-117 (2017).

Wulhfard, et al., "Valproic acid enhances recombinant mRNA and protein levels in transiently transfected Chinese hamster ovary cells," Journal of Biotechnology, pp. 128-132 (2010).

International Search Report and Written Opinion of the ISA for PCT/US2019/045926, mailed Nov. 11, 2019, 11 pgs.

Asokan et al., "The AAV vector toolkit: poised at the clinical crossroads", Mol. Ther. 20(4);699-708 (2012).

Zinn, et al., "In Silico Reconstruction of the Viral Evolutionary Lineage Yields a Potent Gene Therapy Vector", Cell Rep. 12(6):1056-1068 (2015).

Georgiadis et al., "Development of an optimized AAV2/5 gene therapy vector for Leber congenital amaurosis owing to defects in RPE65", Gene Therapy 23: 857-862 (2016).

Georgiadis et al., "Correction: Development of an optimized AAV2/5 gene therapy vector for Leber congenital amaurosis owing to defects in RPE65" Gene Therapy 25(6): 450 (2018).

Puzzo et al., "Rescue of Pompe disease in mice by AAV-mediated liver delivery of secretable acid α-glucosidase", Sci. Transl. Med. 29(9): 418 (2017).

Duan et al., "Enhancement of Muscle Gene Delivery with Pseudotyped Adeno-Associated Virus Type 5 Correlates with Myoblast Differentiation", J. Virol., 75(16):7662-7671 (2001).

Halbert et al., "Repeat Transduction in the Mouse Lung by Using Adeno-Associated Virus Vectors with Different Serotypes", J. Virol., 74(3):1524-1532 (2000).

Zolotukhin et al., "Production and purification of serotype 1, 2, and 5 recombinant adeno-associated viral vectors", Methods 28(2):158-167 (2002).

Auricchio et al., "Exchange of surface proteins impacts on viral vector cellular specificity and transduction characteristics: the retina as a model" Hum. Molec. Genet. 10(26): 3075-3081, (2001).

Wu et al., "Self-complementary recombinant adeno-associated viral vectors: packaging capacity and the role of rep proteins in vector purity", Human Gene Therapy, 18(2):171-82 (2007).

McCarty et al., "Self-complementary recombinant adeno-associated virus (scAAV) vectors promote efficient transduction independently of DNA synthesis", Gene Therapy, 8(6): 1248-1254 (2001).

(56)  References Cited

OTHER PUBLICATIONS

Brument et al., "A versatile and scalable two-step ion-exchange chromatography process for the purification of recombinant adeno-associated virus serotypes-2 and -5", Mol. Therapy 6(5): 678-686 (2002).

Gao et al., "Purification of Recombinant Adeno-Associated Virus Vectors by col. Chromatography and Its Performance in Vivo", Hum. Gene Therapy 11(15): 2079-2091 (2000).

Paul et al., "Increased Viral Titer Through Concentration of Viral Harvests from Retroviral Packaging Lines", Human Gene Therapy 4(5): 609-615 (1993).

Grieger et al., "Production of Recombinant Adena-associated Virus Vectors Using Suspension HEK293 Cells and Continuous Harvest of Vector From the Culture Media for GMP FIX and FL T1 Clinical Vector", Molecular Therapy: The Journal of The American Society of Gene Therapy, vol. 24, No. 2, Feb. 1, 2016, pp. 287-297.

* cited by examiner

Figure 1

| Factor | Level 1 | Level 2 | Level 3 |
|---|---|---|---|
| Sodium Chloride (mM) | 0 | 30 | 60 |
| Sodium Valproate (mM) | 0 | 1 | 2 |
| Time of NaCl Addition (hours post-transfection) | 4 | 24 | 48 |
| Time of NaVal Addition (hours post-transfection) | 4 | 24 | 48 |

| Condition | Vessel Number | Sodium Chloride (mM) | Sodium Valproate (mM) | Time of NaCl (hpt) | Time of NaVal (hpt) | Virus Yield (×1e10 gc/mL) |
|---|---|---|---|---|---|---|
| 1 | 1-1 | 60 | 0 | 48 | 48 | 9.1 |
| 2 | 1-2 | 60 | 2 | 4 | 24 | 11 |
| 3 | 1-3 | 60 | 1 | 4 | 48 | 11 |
| 4 | 1-4 | 0 | 2 | 48 | 24 | 8.4 |
| 5 | 1-5 | 60 | 0 | 4 | 4 | 9.9 |
| 6 | 1-6 | 30 | 2 | 24 | 4 | 14 |
| 7 | 1-7 | 0 | 0 | 48 | 48 | 0.93 |
| 8 | 1-8 | 30 | 2 | 48 | 48 | 0.31 |
| 9 | 1-9 | 60 | 2 | 24 | 48 | 9.4 |
| 10 | 1-10 | 0 | 0 | 48 | 4 | 6.7 |
| 11 | 1-11 | 30 | 1 | 4 | 4 | 11 |
| 12 | 1-12 | 0 | 1 | 24 | 48 | 7 |
| 13 | 3-1 | 60 | 1 | 48 | 24 | 4.5 |
| 14 | 3-2 | 60 | 2 | 48 | 4 | 8.8 |
| 15 | 3-3 | 0 | 2 | 4 | 48 | 5.7 |
| 16 | 3-4 | 60 | 0 | 48 | 4 | 6.4 |
| 17 | 3-5 | 0 | 2 | 4 | 4 | 0.015 |
| 18 | 3-6 | 30 | 0 | 24 | 24 | 6.8 |
| 19 | 3-7 | 60 | 2 | 4 | 4 | 8.5 |
| 20 | 3-8 | 0 | 2 | 48 | 4 | 7.7 |
| 21 | 3-9 | 0 | 0 | 4 | 4 | 5 |
| 22 | 3-10 | 30 | 2 | 4 | 48 | 7.2 |
| 23 | 3-11 | 0 | 0 | 4 | 48 | 5.3 |
| 24 | 3-12 | 60 | 0 | 4 | 48 | 6.6 |

SCALABLE METHOD FOR RECOMBINANT AAV PRODUCTION

CROSS-REFERENCE TO RELATED APPLICATIONS

This application is the U.S. national phase of International Application No. PCT/US2019/045926 filed Aug. 9, 2019 which designated the U.S. and claims priority of U.S. Provisional Application No. 62/717,212 filed Aug. 10, 2018, the entire content of each of which is incorporated herein in its entirety.

BACKGROUND

Recombinant Adeno-Associated Virus (rAAV)-based vectors are currently the most widely used gene therapy products in development. The preferred use of rAAV vector systems is due, in part, to the lack of disease associated with the wild-type virus, the ability of AAV to transduce non-dividing as well as dividing cells, and the resulting long-term robust transgene expression observed in clinical trials and that indicate great potential for delivery in gene therapy indications. Additionally, different naturally occurring AAV and recombinant AAV vector serotypes, specifically target different tissues, organs, and cells, and help evade any pre-existing immunity to the vector, thus expanding the therapeutic applications of AAV-based gene therapies.

Histone deacetylase (HDAC) inhibitors have been used in transfection protocols for the expression of proteins in recombinant animal cell culture. For example, Vazquez-Lombardi exemplified the use of HDAC inhibitors ("Enhancer 1 and 2") as a co-transfection reagent with plasmids expressing IgG, and additionally the enhancers were added to the culture on the second day (Vazquez-Lombardi et al., Nature Protocols, 13(1): 99-117 (2018), published online 14 Dec. 2017). WO2013166339A1 describes the use of Enhancer 1 (valproic acid) and Enhancer 2 (sodium propionate) in small culture conditions less than 50 L, observing that Enhancer 2 has no strong effect alone, but in combination with Enhancer 1 may provide a benefit to recombinant IgG production. Chun reported that the use of propionic and butyric acids enhanced production of recombinant B-domain deleted factor VIII by CHO cells, however both of the alkanoic acids inhibited cell growth and rFVIII production was maximal at about 3.5 days (Chun et al., Biotechnology Letters, 25: 315-319 (2003)). Cervera reports the use of a mixture of transfection enhancers to increase production of a virus-like particles comprising a single recombinant polypeptide (e.g. a Gag-like virus-like particle) in HEK293 suspension cell cultures (Cervera et al, Appl. Microbiol. Biotechnol., 99: 9935-9949 (2015)). None of these reports, however, disclose the use of Histone deacetylase (HDAC) inhibitors to increase recombinant production of viral particles encapsidating a genome, e.g., cultured cells expressing rAAV particles comprising multiple polypeptides and a nucleotide genome.

Tiernan and Tipper discloses the use of trichostatin A, an HDAC inhibitor in a method for generating stable cell lines comprising rAAV transgenes (WO 2018/175775). Tiernan and Tipper discloses that methods comprising co-transfection of a recombinant viral vector with an HDAC inhibitor may enhance the integration of the viral vector into the host cell genome and increase the yield of viral vector harvested from the host cell. Tiernan and Tipper discloses using the stable cell lines in the production of rAAV particles, however, does not teach or suggest the use of an HDAC inhibitor in the production culture of the rAAV particles.

Before AAV-based gene therapies can be more widely adopted for late clinical stage and commercial use, new methods for large scale GMP compliant production of rAAV particles need to be developed. A major challenge for upstream process development is the establishment of scalable, cost effective, GMP compliant methods for rAAV production. Manufacturing rAAV particles for a single unit dose can cost several $100 k using currently approved methods. Thus, there is a need for GMP compliant scalable processes to produce rAAV particles.

BRIEF SUMMARY

The disclosure provides methods for producing recombinant AAV (rAAV) particles comprising culturing cells capable of producing rAAV particles in the presence of an effective amount of a histone deacetylase (HDAC) inhibitor under conditions that allow the production of the rAAV particles. In some embodiments, the cells are cultured in the presence of the HDAC inhibitor and a sodium salt at a concentration between about 110 mM and 250 mM. In some embodiments, a method disclosed herein encompasses isolating the rAAV particles produced according to a method disclosed herein. In some embodiments, a method disclosed herein encompasses harvesting of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, sterile filtration, or any combination(s) thereof. In some embodiments, a method disclosed herein does not include centrifugation. In some embodiments, a method disclosed herein comprises harvest of a cell culture, clarification of the harvested cell culture by depth filtration, a first sterile filtration, a first tangential flow filtration, affinity chromatography, anion exchange chromatography (e.g., monolith anion exchange chromatography), a second tangential flow filtration, and a second sterile filtration. In some embodiments, a method of isolating rAAV particles produced according to a method disclosed herein comprises clarification of a harvested cell culture by depth filtration, a first sterile filtration, a first tangential flow filtration, affinity chromatography, anion exchange chromatography (e.g., monolith anion exchange chromatography), a second tangential flow filtration, and a second sterile filtration.

In some embodiments, the disclosure provides:

[1.] A method of producing rAAV particles, comprising
   (a) providing a cell culture comprising a cell;
   (b) introducing into the cell one or more polynucleotides encoding at least one of
      i. an rAAV genome to be packaged,
      ii. adenovirus helper functions necessary for packaging,
      iii. an AAV rep protein sufficient for packaging, and
      iv. an AAV cap protein sufficient for packaging;
   (c) adding to the cell culture an HDAC inhibitor to a final concentration between about 0.1 mM and about 20 mM;
   (d) maintaining the cell culture under conditions that allow production of the rAAV particles for between about 2 days and about 15 days after (b).

[2.] The method of [2], wherein the HDAC inhibitor is a short-chain fatty acid or salt thereof.

[3.] The method of [1] or [2], wherein the HDAC inhibitor is valproate, propionate, butyrate, or a salt thereof.

[4.] The method of [3], wherein the HDAC inhibitor is sodium valproate.

[5.] The method of [3], wherein the HDAC inhibitor is sodium propionate.

[6.] The method of any one of [1] to [5], wherein the cell culture has a final HDAC inhibitor concentration between about 0.5 mM and about 5 mM.

[7.] The method of any one of [1] to [5], wherein the cell culture has a final HDAC inhibitor concentration between about 0.5 mM and about 3 mM.

[8.] The method of any one of [1] to [7], wherein the HDAC inhibitor is added after step b).

[9.] The method of [8], wherein the HDAC inhibitor is added between about 1 hour and about 48 hours after step b).

[10.] The method of [8], wherein the HDAC inhibitor is added between about 12 hours and about 36 hours after step b).

[11.] The method of [8], wherein the HDAC inhibitor is added between about 18 hours and about 30 hours after step b).

[12.] The method of [8], wherein the HDAC inhibitor is added less than about 48 hours after step b).

[13.] The method of [8], wherein the HDAC inhibitor is added less than about 36 hours after step b).

[14.] The method of [8], wherein the HDAC inhibitor is added at least about 6 hours after step b).

[15.] The method of [8], wherein the HDAC inhibitor is added at least about 12 hours after step b).

[16.] The method of [8], wherein the HDAC inhibitor is added about 6 hours, about 9 hours, about 12 hours, about 18 hours, about 20 hours, about 24 hours, about 30 hours, about 36 hours, or about 48 hours after step b).

[17.] The method of [8], wherein the HDAC inhibitor is added about 20 hours after step b).

[18.] The method of [8], wherein the HDAC inhibitor is added about 24 hours after step b).

[19.] The method of any one of [1] to [18], further comprising adding to the culture a sodium salt in sufficient amount to increase the final concentration of the sodium salt by between about 20 mM and about 150 mM.

[20.] The method of [19], wherein the final concentration of the sodium salt is increased by between about 20 mM and about 50 mM, between about 40 mM and about 80 mM, or between about 70 mM and 120 about mM.

[21.] The method of [19], wherein the final concentration of the sodium salt is increased by between about 40 mM and about 140 mM.

[22.] The method of any one of [1] to [21], further comprising adding to the culture a sodium salt in sufficient amount to increase the final concentration of the sodium salt to between about 120 mM and about 250 mM.

[23.] The method of [22], wherein the final concentration of the sodium salt is between about 130 mM and about 160 mM, between about 150 mM and about 190 mM, or between about 180 mM and about 240 mM.

[24.] The method of [22], wherein the final concentration of the sodium salt is between about 150 mM and about 240 mM.

[25.] The method of [22], wherein prior to adding the sodium salt, the cell culture comprises between about 90 mM and about 120 mM NaCl.

[26.] The method of any one of [19] to [25], wherein the sodium salt is sodium chloride.

[27.] The method of any one of [19] to [26], wherein the HDAC inhibitor and the sodium salt are added separately in any order.

[28.] The method of any one of [19] to [27], wherein the sodium salt is added before b).

[29.] The method of any one of [19] to [27], wherein the sodium salt is added after b).

[30.] The method of any one of [19] to [29], wherein the sodium salt is added after adding the HDAC inhibitor.

[31.] The method of [30], wherein the sodium salt is added between about 5 minutes and about 6 hours after adding the HDAC inhibitor.

[32.] The method of [30], wherein the sodium salt is added between about 20 minutes and about 2 hours after adding the HDAC inhibitor.

[33.] The method of [30], wherein the sodium salt is added less than about 2 hours after adding the HDAC inhibitor.

[34.] The method of [30], wherein the sodium salt is added less than about 1 hour after adding the HDAC inhibitor.

[35.] The method of [30], wherein the sodium salt is added at least about 5 minutes after adding the HDAC inhibitor.

[36.] The method of [30], wherein the sodium salt is added at least about 20 minutes after adding the HDAC inhibitor.

[37.] The method of any one of [1] to [36], wherein the cell culture is maintained for about 2 days, about 3 days, about 4 days, about 5 days, about 6 days, or about 7 days after b).

[38.] The method of [37], wherein the cell culture is maintained for about 5 days after b).

[39.] The method of any one of [1] to [38], comprising introducing into the cell one or more polynucleotides encoding
   i. an rAAV genome to be packaged,
   ii. adenovirus helper functions necessary for packaging,
   iii. an AAV rep protein sufficient for packaging, and
   iv. an AAV cap protein sufficient for packaging.

[40.] The method of any one of [1] to [39], wherein the adenovirus helper functions comprise at least one of an adenovirus Ela gene, Elb gene, E4 gene, E2a gene, and VA gene.

[41.] The method of any one of [1] to [40], wherein the introducing one or more polynucleotides into the cell is by transfection.

[42.] The method of any one of [1] to [41], wherein the cell is a mammalian cell.

[43.] The method of any one of [1] to [41], wherein the cell is an insect cell.

[44.] The method of any one of [1] to [41], wherein the cell is a HEK293 cell, HEK derived cell, CHO cell, CHO derived cell, HeLa cell, SF-9 cell, BHK cell, Vero cell, or PerC6 cell.

[45.] The method of any one of [1] to [41], wherein the cell is a HEK293 cell.

[46.] The method of any one of [1] to [45], wherein the cell culture is a suspension culture.

[47.] The method of any one of [1] to [46], further comprising recovering the rAAV particles.

[48.] The method of any one of [1] to [47], wherein the cell culture produces greater than 5×10e+10 GC/ml rAAV particles.

[49.] The method of any one of [1] to [48], wherein the cell culture produces at least about twice as many rAAV particles measured as GC/ml than a culture in the absence of adding of the HDAC inhibitor and sodium salt.

[50.] The method of any one of [1] to [49], wherein the cell culture has a volume between about 50 liters and about 20,000 liters.

[51.] A method for producing rAAV particles, comprising (a) providing a cell culture comprising a cell capable of producing rAAV;

(b) adding to the cell culture an HDAC inhibitor to a final concentration between about 0.1 mM and about 20 mM; and (c) maintaining the cell culture under conditions that allows production of the rAAV particles.

[52.] The method of [51], wherein the HDAC inhibitor is a short-chain fatty acid or salt thereof.

[53.] The method of [52], wherein the HDAC inhibitor is valproate, propionate, butyrate, or a salt thereof.

[54.] The method of [53], wherein the HDAC inhibitor is sodium propionate.

[55.] The method of [53], wherein the HDAC inhibitor is sodium valproate.

[56.] The method of any one of [51] to [55], wherein the cell culture has a final HDAC inhibitor concentration between about 0.5 mM and about 5 mM.

[57.] The method of any one of [51] to [55], wherein the cell culture has a final HDAC inhibitor concentration between about 0.5 mM and about 3 mM.

[58.] The method of any one of [51] to [57], further comprising adding to the culture a sodium salt in sufficient amount to increase the final concentration of the sodium salt by between about 20 mM and 150 mM.

[59.] The method of [58], wherein the final concentration of the sodium salt is increased by between about 20 mM and about 50 mM, between about 40 mM and about 80 mM, or between about 70 mM and about 120 mM.

[60.] The method of [58], wherein the final concentration of the sodium salt is increased by between about 40 mM and about 140 mM.

[61.] The method of any one of [51] to [60], further comprising adding to the culture a sodium salt in sufficient amount to increase the final concentration of the sodium salt to between about 120 mM and about 250 mM.

[62.] The method of [61], wherein the final concentration of the sodium salt is between about 130 mM and about 160 mM, between about 150 mM and about 190 mM, or between about 180 mM and about 240 mM.

[63.] The method of [61], wherein the final concentration of the sodium salt is between about 150 mM and about 240 mM.

[64.] The method of any one of [51] to [63], wherein prior to adding the sodium salt, the cell culture comprises between about 90 mM and about 120 mM NaCl.

[65.] The method of any one of [51] to [64], wherein the sodium salt is sodium chloride.

[66.] The method of any one of [51] to [65], wherein the HDAC inhibitor and the sodium salt are added separately in any order.

[67.] The method of [66], wherein the sodium salt is added after adding the HDAC inhibitor.

[68.] The method of [67], wherein the sodium salt is added between about 5 minutes and about 6 hours after adding the HDAC inhibitor.

[69.] The method of [67], wherein the sodium salt is added between about 20 minutes and about 2 hours after adding the HDAC inhibitor.

[70.] The method of [67], wherein the sodium salt is added less than about 2 hours after adding the HDAC inhibitor.

[71.] The method of [67], wherein the sodium salt is added less than about 1 hour after adding the HDAC inhibitor.

[72.] The method of [67], wherein the sodium salt is added at least about 5 minutes after adding the HDAC inhibitor.

[73.] The method of [67], wherein the sodium salt is added at least about 20 minutes after adding the HDAC inhibitor.

[74.] The method of any one of [51] to [73], wherein the cell culture is maintained under conditions that allow production of the rAAV particles for between about 2 days and about 10 days or between about 5 days and 14 days after b).

[75.] The method of any one of [51] to [73], wherein the cell culture is maintained for about 2 days, about 3 days, about 4 days, about 5 days, about 6 days, or about 7 days after b).

[76.] The method of [75], wherein the cell culture is maintained for about 5 days after b).

[77.] A method for producing rAAV particles, comprising culturing a cell capable of producing rAAV particles in a medium comprising between about 0.1 mM and about 20 mM of an HDAC inhibitor under conditions that allow the production of the rAAV particles.

[78.] The method of [77], wherein the HDAC inhibitor is a short-chain fatty acid or salt thereof.

[79.] The method of [78], wherein the HDAC inhibitor is valproate, propionate, butyrate, or a salt thereof.

[80.] The method of [79], wherein the HDAC inhibitor is sodium valproate.

[81.] The method of [79], wherein the HDAC inhibitor is sodium propionate.

[82.] The method of any one of [77] to [81], wherein the medium comprises between about 0.5 mM and about 5 mM of the HDAC inhibitor.

[83.] The method of any one of [77] to [81], wherein the medium comprises between about 0.5 mM and about 3 mM of the HDAC inhibitor.

[84.] The method of any one of [77] to [83], wherein the medium further comprises between about 120 mM and about 250 mM sodium chloride.

[85.] The method of any one of [77] to [83], wherein the medium further comprises between about 130 mM and about 160 mM, between about 150 mM and about 190 mM, or between about 180 mM and about 240 mM NaCl sodium chloride.

[86.] The method of any one of [77] to [83], wherein the medium further comprises between about 150 mM and about 240 mM sodium chloride.

[87.] The method of any one of [51] to [86], wherein the cell capable of producing rAAV has been transfected with one or more polynucleotides encoding at least one of (a) an rAAV genome to be packaged, (b) adenovirus helper functions necessary for packaging,

(c) an AAV rep protein sufficient for packaging, and (d) an AAV cap protein sufficient for packaging.

[88.] The method of any one of [51] to [86], wherein the cell capable of producing rAAV has been transfected with one or more polynucleotides encoding (a) an rAAV genome to be packaged, (b) adenovirus helper functions necessary for packaging, (c) an AAV rep protein sufficient for packaging, and (d) an AAV cap protein sufficient for packaging.

[89.] The method of any one of [51] to [88], wherein the cell is a mammalian cell or an insect cell.

[90.] The method of any one of [51] to [88], wherein the cell is a HEK293 cell, HeLa cell, SF-9 cell, BHK cell, Vero cell, or PerC6 cell, optionally wherein the cell is a HEK293 cell.

[91.] The method of any one of [51] to [90], wherein the cell culture is a suspension culture.

[92.] The method of any one of [77] to [91], wherein the culturing under conditions that allow production of the rAAV particles is for between about 2 days and about 10 days or between about 5 days and 14 days.

[93.] The method of any one of [77] to [91], wherein the culturing under conditions that allow production of the rAAV particles is for about 2 days, about 3 days, about 4 days, about 5 days, about 6 days, or about 7 days.

[94.] The method of [93], wherein the culturing under conditions that allow production of the rAAV particles is for about 5 days.

[95.] The method of any one of [51] to [94], further comprising recovering the rAAV particles.

[96.] The method of any one of [51] to [95], wherein the cell culture produces between about 5×10e+10 GC/ml and about 1×10e+12 GC/ml rAAV particles.

[97.] The method of any one of [51] to [96], wherein the cell culture produces at least about twice as many rAAV particles measured as GC/ml than a culture in the absence of adding of the HDAC inhibitor and sodium salt.

[98.] A method of increasing the production of rAAV particles, comprising (a) providing a cell culture comprising a cell;

(b) introducing into the cell one or more polynucleotides encoding at least one of i. an rAAV genome to be packaged, ii. adenovirus helper functions necessary for packaging, iii. an AAV rep protein sufficient for packaging, and iv. an AAV cap protein sufficient for packaging;

(c) adding to the cell culture an HDAC inhibitor to a final concentration between about 0.1 mM and about 20 mM; and (d) maintaining the cell culture under conditions that allow production of the rAAV particles for between about 2 days and about 15 days after (b).

[99.] The method of [98], wherein the HDAC inhibitor is sodium valproate.

[100.] The method of [98], wherein the HDAC inhibitor is sodium propionate.

[101.] The method of any one of [98] to [100], further comprising adding to the culture a sodium salt in sufficient amount to increase the final concentration of the sodium salt by between about 40 mM and about 150 mM.

[102.] The method of any one of [98] to [101], wherein the sodium salt is sodium chloride.

[103.] A method of increasing the production of rAAV particles, comprising (a) providing a cell culture comprising a cell capable of producing rAAV;

(b) adding to the cell culture an HDAC inhibitor to a final concentration between about 0.1 mM and about 20 mM; and (c) maintaining the cell culture under conditions that allows production of the rAAV particles.

[104.] The method of [103], wherein the HDAC inhibitor is sodium valproate.

[105.] The method of [103], wherein the HDAC inhibitor is sodium propionate.

[106.] The method of any one of [103] to [105], further comprising adding to the culture a sodium salt in sufficient amount to increase the final concentration of the sodium salt to between about 120 mM and about 250 mM.

[107.] The method of any one of [103] to [106], wherein the sodium salt is sodium chloride.

[108.] The method of any one of [103] to [107], wherein the cell culture is maintained under conditions that allow production of the rAAV particles for between about 2 days and about 10 days or between about 5 days and 14 days after b).

[109.] The method of any one of [103] to [107], wherein the cell culture is maintained for about 2 days, about 3 days, about 4 days, about 5 days, about 6 days, or about 7 days after b).

[110.] The method of [109], wherein the cell culture is maintained for about 5 days after b).

[111.] A method of increasing the production of rAAV particles, comprising culturing a cell capable of producing rAAV particles in a medium comprising between about 0.1 mM and about 20 mM of an HDAC inhibitor under conditions that allow the production of the rAAV particles.

[112.] The method of [111], wherein the HDAC inhibitor is sodium valproate.

[113.] The method of [111], wherein the HDAC inhibitor is sodium propionate.

[114.] The method of any one of [111] to [113], wherein the medium further comprises between about 120 mM and about 250 mM sodium chloride.

[115.] The method of any one of [1] to [114], wherein the rAAV particles comprise a capsid protein of the AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype.

[116.] The method of any one of [1] to [114], wherein the rAAV particles comprise a capsid protein of the AAV8, AAV9, AAV.rh10, AAV.rh20, AAV.rh39, AAV.Rh74, AAV.RHM4-1, or AAV.hu37 serotype.

[117.] The method of any one of [1] to [114], wherein the rAAV particles comprise a capsid protein of the AAV8 or AAV9 serotype.

[118.] The method of any one of [1] to [117], wherein the cell culture has a volume between about 50 liters and about 20,000 liters.

[119.] The method of [118], wherein the cell culture has a volume between about 50 liters and about 5,000 liters.

[120.] The method of [118], wherein the cell culture has a volume between about 50 liters and about 2,000 liters.

[121.] The method of [118], wherein the cell culture has a volume between about 50 liters and about 1,000 liters.

[122.] The method of [118], wherein the cell culture has a volume between about 50 liters and about 500 liters.

[123.] A composition comprising isolated rAAV particles that were produced by the method of any one of [1] to [122.

[124.] The method of any one of [1] to [50] or [98] to [102], wherein the rAAV genome packaged comprises a transgene.

[125.] The method of [124], wherein the transgene comprises a regulatory element operatively connected to a polynucleotide encoding a polypeptide.

[126.] The method of [125], wherein the regulatory element comprises one or more of an enhancer, promoter, and polyA region.

[127.] The method of [125 or [126], wherein the regulatory element and polynucleotide encoding a polypeptide are heterologous.

[128.] The method of any one of [124] to [127], wherein the transgene encodes an anti-VEGF Fab, iduronidase (IDUA), iduronate 2-sulfatase (IDS), low-density lipoprotein receptor (LDLR), tripeptidyl peptidase 1 (TPP1), or non-membrane associated splice variant of VEGF receptor 1 (sFlt-1).

[129.] The method of any one of [124] to [127], wherein the transgene encodes an gamma-sarcoglycan, Rab Escort Protein 1 (REP1/CHM), retinoid isomerohydrolase (RPE65), cyclic nucleotide gated channel alpha 3 (CNGA3), cyclic nucleotide gated channel beta 3 (CNGB3), aromatic L-amino acid decarboxylase (AADC), lysosome-associated membrane protein 2 isoform B (LAMP2B), Factor VIII, Factor IX, retinitis pigmentosa GTPase regulator (RPGR), retinoschisin (RS1), sarcoplasmic reticulum calcium ATPase (SERCA2a), aflibercept, battenin (CLN3), transmembrane ER protein (CLN6), glutamic acid decarboxylase (GAD), Glial cell line-derived neurotrophic factor (GDNF), aquaporin 1 (AQP1), dystrophin, myotubularin 1 (MTM1), follistatin (FST), glucose-6-phosphatase (G6Pase), apolipoprotein A2 (APOA2), uridine diphosphate glucuronosyl transferase 1A1 (UGT1A1), arylsulfatase B (ARSB), N-acetyl-alpha-glucosaminidase (NAGLU), alpha-glucosidase (GAA), alpha-galactosidase (GLA), beta-galactosidase (GLB1), lipoprotein lipase (LPL), alpha 1-antitrypsin (AAT), phosphodiesterase 6B (PDE6B), ornithine carbamoyltransferase 90TC), survival motor neuron (SMN1), survival motor neuron (SMN2), neurturin (NRTN), Neurotrophin-3 (NT-3/NTF3), porphobilinogen deaminase (PBGD), nerve growth factor (NGF), mitochondrially encoded NADH:ubiquinone oxidoreductase core subunit 4 (MT-ND4), protective protein cathepsin A (PPCA), dysferlin, MER proto-oncogene, tyrosine kinase (MERTK), cystic fibrosis transmembrane conductance regulator (CFTR), or tumor necrosis factor receptor (TNFR)-immunoglobulin (IgG1) Fc fusion.

In some embodiments, a method disclosed herein further comprises downstream processing of the rAAV particles produced according to the method of any one of [1] to [129]. In some embodiments, the downstream processing is at least one of harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, sterile filtration. In further embodiments, the upstream processing includes at least 2, at least 3, at least 4, at least 5, or at least 6 of harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, and sterile filtration. In some embodiments, the downstream processing does not include centrifugation of the harvested cell culture.

BRIEF DESCRIPTION OF THE DRAWINGS

FIG. 1. Recombinant virus yields obtained following the addition of sodium chloride, and/or sodium valproate. Final concentration of the reagents added is shown. The base medium included ~100 mM sodium chloride but no sodium valproate.

DETAILED DESCRIPTION

Figure 2:
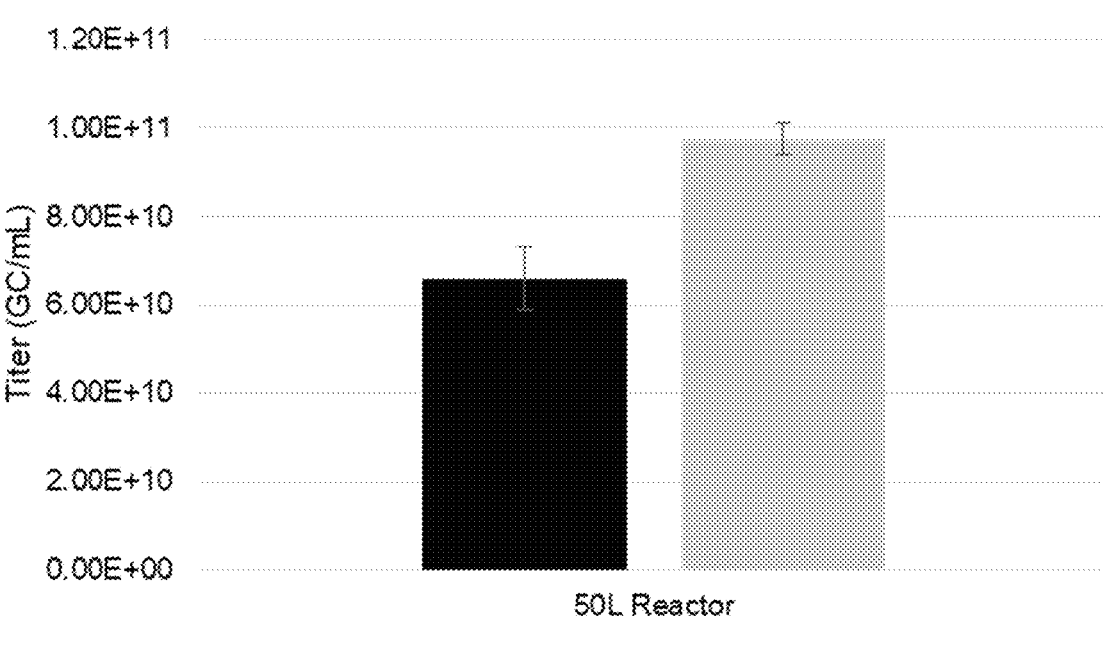
FIG. 2. Virus yield from large scale production of rAAV8 particles using NaCl and sodium propionate.

In some embodiments, the disclosure provides methods for producing rAAV particles by culturing cells capable of producing rAAV particles in the presence of an effective amount of an histone deacetylase (HDAC) inhibitor under conditions in which the rAAV particles are produced. In some embodiments, the cells are cultured in the presence of the HDAC inhibitor and a sodium salt at a concentration between about 110 mM and 250 mM. The rAAV particles produced by a method disclosed herein are suitable for further downstream processing, for example, by harvesting and purifying the rAAV particles using, to produce isolated rAAV particles and compositions, for example, pharmaceutical compositions comprising thereof. The described methods provide flexible, cost-effective, commercially scalable processes consistent with GMP regulatory requirements for producing rAAV particles for use in gene therapy applications. Methods described herein are suited to any rAAV serotype, including without limitation AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16, and derivatives, modifications, or pseudotypes thereof. In some embodiments, the methods are used to produce rAAV8 particles. In some embodiments, the methods are used to produce rAAV8 derivative particles, rAAV8 modification particles, or rAAV8 pseudotype particles. In some embodiments, the methods are used to produce rAAV9 particles. In some embodiments, the methods are used to produce rAAV9 derivative particles, rAAV9 modification particles, or rAAV9 pseudotype particles.

The inventors have surprisingly found that methods disclosed herein provide a two-fold or higher increase in rAAV yield. These results could not have been expected based on earlier findings that HDAC inhibitors can increase the expression of recombinant polypeptides in transfected cells. Cellular production of AAV particles requires the assembly of three capsid proteins and a single stranded nucleotide genome into a functional viral unit. There was no reason to believe that HDAC inhibitors would be able to simultaneously increase the production of all AAV components, including the production of the AAV genome. And there was no reason to believe that the host cell machinery was capable of assembling increased number of AAV particles even if the HDAC inhibitor increased the production of the viral polypeptides. Cervera's report that transfection enhancers can increase the production of virus-like particles (VLP) also did not give a reason to believe that HDAC inhibitors can increase the production of rAAV particles in a host cell because the VLPs comprised a single gag protein and no genome. Cervera et al, Appl. Microbiol. Biotechnol., 99: 9935-9949 (2015). Thus, production of the VLPs did not require assembly of multiple polypeptides and a nucleotide genome.

Given the very high number of rAAV particles needed to prepare a single unit dose, a two-fold or higher increase in rAAV yield provides a significant reduction in the cost of goods per unit dose. Increased virus yield allows a corresponding reduction not only in the cost of consumables needed to produce AAV particles, but also in the cost of capital expenditure in connection with building industrial virus purification facilities.

Definitions

Unless defined otherwise, all technical and scientific terms used herein have the same meaning as commonly understood by one of ordinary skill in the art to which this disclosure is related. To facilitate an understanding of the disclosed methods, a number of terms and phrases are defined below.

"About" modifying, for example, the quantity of an ingredient in the compositions, concentration of an ingredient in the compositions, flow rate, rAAV particle yield, feed volume, salt concentration, and like values, and ranges thereof, employed in the methods provided herein, refers to variation in the numerical quantity that can occur, for example, through typical measuring and handling procedures used for making concentrates or use solutions; through inadvertent error in these procedures; through differences in the manufacture, source, or purity of the ingredients employed to make the compositions or carry out the methods; and like considerations. The term "about" also encompasses amounts that differ due to aging of a composition with a particular initial concentration or mixture. The term "about" also encompasses amounts that differ due to mixing or processing a composition with a particular initial concentration or mixture. Whether or not modified by the term "about" the claims include equivalents to the quantities. In some embodiments, the term "about" refers to ranges of approximately 10-20% greater than or less than the indicated number or range. In further embodiments, "about" refers to plus or minus 10% of the indicated number or range. For example, "about 10%" indicates a range of 9% to 11%.

"AAV" is an abbreviation for adeno-associated virus, and may be used to refer to the virus itself or modifications, derivatives, or pseudotypes thereof. The term covers all subtypes and both naturally occurring and recombinant forms, except where required otherwise. The abbreviation "rAAV" refers to recombinant adeno-associated virus. The term "AAV" includes AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), avian AAV, bovine AAV, canine AAV, equine AAV, primate AAV, non-primate AAV, and ovine AAV, and modifications, derivatives, or pseudotypes thereof. "Primate AAV" refers to AAV that infect primates, "non-primate AAV" refers to AAV that infect non-primate mammals, "bovine AAV" refers to AAV that infect bovine mammals, etc. In some embodiments, the AAV particle is AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16. In some embodiments, the rAAV particle is a derivative, modification, or pseudotype of AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

"Recombinant", as applied to an AAV particle means that the AAV particle is the product of one or more procedures that result in an AAV particle construct that is distinct from an AAV particle in nature.

A recombinant Adeno-associated virus particle "rAAV particle" refers to a viral particle composed of at least one AAV capsid protein and an encapsidated polynucleotide rAAV vector comprising a heterologous polynucleotide (i.e. a polynucleotide other than a wild-type AAV genome such as a transgene to be delivered to a mammalian cell). The rAAV particle may be of any AAV serotype, including any modification, derivative or pseudotype (e.g., AAV1, AAV2, AAV3, AAV4, AAV5, AAV6, AAV7, AAV8, AAV9, or AAV10, or derivatives/modifications/pseudotypes thereof). Such AAV serotypes and derivatives/modifications/pseudotypes, and methods of producing such serotypes/derivatives/modifications/pseudotypes are known in the art (see, e.g., Asokan et al., Mol. Ther. 20(4):699-708 (2012). In some embodiments, the rAAV particles comprise a capsid protein from an AAV capsid serotype selected from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise a capsid protein that is a derivative, modification, or pseudotype of AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 capsid protein.

The rAAV particles of the disclosure may be of any serotype, or any combination of serotypes, (e.g., a population of rAAV particles that comprises two or more serotypes, e.g., comprising two or more of rAAV2, rAAV8, and rAAV9 particles). In some embodiments, the rAAV particles are rAAV1, rAAV2, rAAV3, rAAV4, rAAV5, rAAV6, rAAV7, rAAV8, rAAV9, rAAV10, or other rAAV particles, or combinations of two or more thereof). In some embodiments, the rAAV particles are rAAV8 or rAAV9 particles. In some embodiments, the rAAV particles comprise a capsid protein from two or more serotype selected from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise a capsid protein that is a derivative, modification, or pseudotype of two or more serotype selected from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16 capsid protein.

In some embodiments, the rAAV particles have an AAV capsid protein of a serotype selected from the group consisting of AAV1, AAV2, AAV3, AAV4, AAV5, AAV6, AAV7, AAV8, AAV9, AAV10, AAV11, AAV12, AAV13, AAV14, AAV15 and AAV16 or a derivative, modification, or pseudotype thereof. In some embodiments, the rAAV particles have an AAV capsid protein of a serotype of AAV8, AAV9, or a derivative, modification, or pseudotype thereof. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37.

The term "cell culture," refers to cells grown adherent or in suspension, bioreactors, roller bottles, hyperstacks, microspheres, macrospheres, flasks and the like, as well as the components of the supernatant or suspension itself, including but not limited to rAAV particles, cells, cell debris, cellular contaminants, colloidal particles, biomolecules, host cell proteins, nucleic acids, and lipids, and flocculants. Large scale approaches, such as bioreactors, including suspension cultures and adherent cells growing attached to microcarriers or macrocarriers in stirred bioreactors, are also encompassed by the term "cell culture." Cell culture procedures for both large and small-scale production of proteins are encompassed by the present disclosure.

The terms "purifying", "purification", "separate", "separating", "separation", "isolate", "isolating", or "isolation", as used herein, refer to increasing the degree of purity of rAAV particles from a sample comprising the target product and one or more impurities. Typically, the degree of purity of the target product is increased by removing (completely or partially) at least one impurity from the sample. In some embodiments, the degree of purity of the rAAV in a sample is increased by removing (completely or partially) one or more impurities from the sample by using a method described herein.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Where embodiments of the disclosure are described in terms of a Markush group or other grouping of alternatives, the disclosed method encompasses not only the entire group listed as a whole, but also each member of the group individually and all possible subgroups of the main group, and also the main group absent one or more of the group members. The disclosed methods also envisage the explicit exclusion of one or more of any of the group members in the disclosed methods.

Methods for rAAV Production

In some embodiments, the disclosure provides methods for the production of rAAV particles, comprising (a) providing a cell culture comprising a cell capable of producing rAAV; (b) adding to the cell culture a histone deacetylase (HDAC) inhibitor to a final concentration between about 0.1 mM and about 20 mM; and (c) maintaining the cell culture under conditions that allows production of the rAAV particles. In some embodiments, the HDAC inhibitor comprises a short-chain fatty acid or salt thereof. In some embodiments, the HDAC inhibitor comprises butyrate (e.g., sodium butyrate), valproate (e.g., sodium valproate), propionate (e.g., sodium propionate), or a combination thereof. In some embodiments, after adding the HDAC inhibitor, the cell culture comprises between about 0.5 mM and about 10 mM of butyrate (e.g., sodium butyrate), valproate (e.g., sodium valproate), or propionate (e.g., sodium propionate). In some embodiments, the cell culture comprises between about 0.5 mM and about 5 mM of butyrate (e.g., sodium butyrate). In some embodiments, the cell culture comprises between about 0.5 mM and about 5 mM of valproate (e.g., sodium valproate). In some embodiments, the cell culture comprises between about 0.5 mM and about 5 mM of propionate (e.g., sodium propionate). In some embodiments, the cell culture comprises between about 0.5 mM and about 3 mM of valproate (e.g., sodium valproate). In some embodiments, the cell culture comprises between about 0.5 mM and about 3 mM of propionate (e.g., sodium propionate). In some embodiments, the HDAC inhibitor is added between about 12 hours and about 36 hours after step b). In some embodiments, the method further comprises adding to the culture a sodium salt (e.g., sodium chloride) in sufficient amount to increase the final concentration of the sodium salt by between about 20 mM and 150 mM. In some embodiments, the final concentration of the sodium salt is increased by between about 40 mM and 140 mM. In some embodiments, the final concentration of the sodium salt is between about 150 mM and about 240 mM. In some embodiments, the sodium salt is sodium chloride. In some embodiments, the sodium salt is added after adding the HDAC inhibitor. In some embodiments, the sodium salt is added at least about 20 minutes after adding the HDAC inhibitor. In some embodiments, the method further comprises recovering the rAAV particles. In some embodiments, the cell capable of producing rAAV particles is a HEK293 cell that has been transfected with one or more polynucleotides encoding (i) an rAAV genome to be packaged, (ii) adenovirus helper functions necessary for packaging, (iii) an AAV rep protein sufficient for packaging, and (iv) an AAV cap protein sufficient for packaging. In some embodiments, the cell culture is a suspension culture. In some embodiments, the cell capable of producing rAAV particles is a HEK293 cell that has been transfected with one or more polynucleotides encoding at least one of (i) an rAAV genome to be packaged, (ii) adenovirus helper functions necessary for packaging, (iii) an AAV rep protein sufficient for packaging, and (iv) an AAV cap protein sufficient for packaging. In some embodiments, the cell culture is a suspension culture. In some embodiments, the rAAV particles are AAV8 or AAV9 particles. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37. In some embodiments, the cell culture is maintained under conditions that allow production of the rAAV particles for between about 2 days and about 10 days after step b). In some embodiments, the cell culture is maintained under conditions that allow production of the rAAV particles for between about 5 days and about 14 days or more after step b). In some embodiments, the cell culture is maintained under conditions that allow production of the rAAV particles for continuous harvest.

In some embodiments, the disclosure provides methods for the production of recombinant Adeno-Associated Virus (rAAV) particles comprising (a) providing a cell culture comprising a cell; (b) introducing into the cell one or more polynucleotides encoding at least one of; (i) an rAAV genome to be packaged, (ii) adenovirus helper functions necessary for packaging, (iii) an AAV rep protein sufficient for packaging, and (iv) an AAV cap protein sufficient for packaging; (c) adding to the cell culture an HDAC inhibitor to a final concentration between about 0.1 mM and about 20 mM; and (d) maintaining the cell culture under conditions that allow production of the rAAV particles. In some embodiments, the HDAC inhibitor comprises a short-chain fatty acid or salt thereof. In some embodiments, the HDAC inhibitor comprises butyrate (e.g., sodium butyrate), valproate (e.g., sodium valproate), propionate (e.g., sodium propionate), or a combination thereof. In some embodiments, after adding the HDAC inhibitor, the cell culture comprises between about 0.5 mM and about 10 mM of butyrate (e.g., sodium butyrate), valproate (e.g., sodium valproate), or propionate (e.g., sodium propionate). In some embodiments, the cell culture comprises between about 0.5 mM and about 5 mM of butyrate (e.g., sodium butyrate). In some embodiments, the cell culture comprises between about 0.5 mM and about 5 mM of valproate (e.g., sodium valproate). In some embodiments, the cell culture comprises between about 0.5 mM and about 5 mM of propionate (e.g., sodium propionate). In some embodiments, the cell culture comprises between about 0.5 mM and about 5 mM of butyrate (e.g., sodium butyrate). In some embodiments, the cell culture comprises between about 0.5 mM and about 3 mM of valproate (e.g., sodium valproate). In some embodiments, the cell culture comprises between about 0.5 mM and about 3 mM of propionate (e.g., sodium propionate). In some embodiments, the HDAC inhibitor is added between about 12 hours and about 36 hours after step b). In some embodiments, the method further comprises adding to the culture a sodium salt (e.g., sodium chloride) in sufficient amount to increase the final concentration of the sodium salt by between about 20 mM and 150 mM. In some embodiments, the final concentration of the sodium salt is increased by between about 40 mM and 140 mM. In some embodiments, the final concentration of the sodium salt is between about 150 mM and about 240 mM. In some embodiments, the sodium salt is sodium chloride. In some embodiments, the sodium salt is added to the cell culture after adding the HDAC inhibitor. In some embodiments, the sodium salt is added at least about 20 minutes after adding the HDAC inhibitor. In some embodiments, the method further comprises recovering the rAAV particles. In some embodiments, the cell is a HEK293 cell. In some embodiments, the cell culture is a suspension culture. In some embodiments, the cell is transfected with one or more polynucleotides encoding (i) an rAAV genome to be packaged, (ii) adenovirus helper functions necessary for packaging, (iii) an AAV rep protein sufficient for packaging, and (iv) an AAV cap protein sufficient for packaging. In some embodiments, the cell is transfected with one or more polynucleotides encoding at least one of (i) an rAAV genome to be packaged, (ii) adenovirus helper functions necessary for packaging, (iii) an AAV rep protein sufficient for packaging, and (iv) an AAV cap protein sufficient for packaging. In some embodiments, the rAAV particles are AAV8 or AAV9 particles. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37. In some embodiments, the cell culture is maintained under conditions that allow production of the rAAV particles for between about 2 days and about 10 days after step b). In some embodiments, the cell culture is maintained under conditions that allow production of the rAAV particles for between about 5 days and about 14 days or more after step b). In some embodiments, the cell culture is maintained under conditions that allow production of the rAAV particles for continuous harvest.

In some embodiments, the disclosure provides methods for the production of rAAV particles, comprising culturing a cell capable of producing rAAV particles in a medium comprising between about 0.1 mM and about 20 mM of an HDAC inhibitor under conditions that allow the production of the rAAV particles. In some embodiments, the HDAC inhibitor comprises a short-chain fatty acid or salt thereof. In some embodiments, the HDAC inhibitor comprises butyrate (e.g., sodium butyrate), valproate (e.g., sodium valproate), propionate (e.g., sodium propionate), or a combination thereof. In some embodiments, the medium comprises between about 0.5 mM and about 10 mM of butyrate (e.g., sodium butyrate), valproate (e.g., sodium valproate), or propionate (e.g., sodium propionate). In some embodiments, the medium comprises between about 0.5 mM and about 5 mM of butyrate (e.g., sodium butyrate). In some embodiments, the medium comprises between about 0.5 mM and about 5 mM of valproate (e.g., sodium valproate). In some embodiments, the medium comprises between about 0.5 mM and about 5 mM of propionate (e.g., sodium propionate). In some embodiments, the medium further comprises between about 120 mM and 250 mM of NaCl. In some embodiments, the medium comprises between about 150 mM and about 190 mM, or between about 180 mM and about 240 mM NaCl. In some embodiments, the method further comprises recovering the rAAV particles. In some embodiments, the cell capable of producing rAAV particles is a HEK293 cell that has been transfected with one or more polynucleotides encoding (i) an rAAV genome to be packaged, (ii) adenovirus helper functions necessary for packaging, (iii) an AAV rep protein sufficient for packaging, and (iv) an AAV cap protein sufficient for packaging. In some embodiments, the cell capable of producing rAAV particles is a HEK293 cell that has been transfected with one or more polynucleotides encoding at least one of (i) an rAAV genome to be packaged, (ii) adenovirus helper functions necessary for packaging, (iii) an AAV rep protein sufficient for packaging, and (iv) an AAV cap protein sufficient for packaging. In some embodiments, the cell culture is a suspension culture. In some embodiments, the rAAV particles are AAV8 or AAV9 particles. In some embodiments, the rAAV particles have an AAV capsid protein of a serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have an AAV capsid protein with high sequence homology to AAV8 or AAV9 such as, AAV.rh10, AAV.rh20, AAV.rh39, AAV.Rh74, AAV.RHM4-1, and AAV.hu37. In some embodiments, the cell cultured under conditions that allow production of the rAAV particles for between about 2 days and about 10 days. In some embodiments, the cell cultured under conditions that allow production of the rAAV particles for between about 5 days and about 14 days or more. In some embodiments, the cell culture is maintained under conditions that allow production of the rAAV particles for continuous harvest.

In some embodiments, the disclosure provides methods for increasing the production of rAAV particles. In some embodiments, a method of increasing rAAV production comprises (a) providing a cell culture comprising a cell; (b) introducing into the cell one or more polynucleotides encoding at least one of (i) an rAAV genome to be packaged, (ii) adenovirus helper functions necessary for packaging, (iii) an AAV rep protein sufficient for packaging, and (iv) an AAV cap protein sufficient for packaging; (c) adding to the cell culture an HDAC inhibitor to a final concentration between about 0.1 mM and about 20 mM; and (d) maintaining the cell culture under conditions that allow production of the rAAV particles. In some embodiments, the cell culture is maintained under conditions that allow production of the rAAV particles for between about 2 days and about 10 days after step b). In some embodiments, the cell culture is maintained under conditions that allow production of the rAAV particles for between about 5 days and about 14 days or more after step b). In some embodiments, the cell culture is maintained under conditions that allow production of the rAAV particles for continuous harvest.

In some embodiments, a method of increasing rAAV production comprises culturing a cell capable of producing rAAV particles in a medium comprising between about 0.1 mM and about 20 mM of an HDAC inhibitor under conditions that allow the production of the rAAV particles. In some embodiments, the cell cultured under conditions that allow production of the rAAV particles for between about 2 days and about 10 days. In some embodiments, the cell cultured under conditions that allow production of the rAAV particles for between about 5 days and about 14 days or more after step b). In some embodiments, the cell culture is maintained under conditions that allow production of the rAAV particles for continuous harvest.

In some embodiments, a method of increasing rAAV production comprises (a) providing a cell culture comprising a cell capable of producing rAAV; (b) adding to the cell culture an HDAC inhibitor to a final concentration between about 0.1 mM and about 20 mM; and (c) maintaining the cell culture under conditions that allows production of the rAAV particles. In some embodiments, the cell cultured under conditions that allow production of the rAAV particles for between about 2 days and about 10 days. In some embodiments, the cell cultured under conditions that allow production of the rAAV particles for between about 5 days and about 14 days or more. In some embodiments, the cell culture is maintained under conditions that allow production of the rAAV particles for continuous harvest.

A skilled artisan understands that any histone deacetylase (HDAC) inhibitor compound can be used in a method disclosed herein. HDAC inhibitors are an art recognized class of compounds. See, e.g., Eckschlager et al., Int. J. Mol. Sci. 18, 1414; doi:10.3390/ijms18071414 (2017); Huber et al., The Journal of Biological Chemistry, 286(25):22211-22218 (2011). In some embodiments, the HDAC inhibitor comprises an HDAC isoform-selective inhibitor. In some embodiments, the HDAC inhibitor selectively inhibits the activity of one or more Class I, II, III and IV HDACs. In some embodiments, the HDAC inhibitor inhibits the activity of one or more HDACs from Class I and Class II. In some embodiments, the HDAC inhibitor comprises a pan-inhibitor. In some embodiments, the HDAC inhibitor comprises a hydroxamic acid, short-chain fatty acid, benzamide, cyclic tetrapeptide, or a sirtuin inhibitor. In some embodiments, the HDAC inhibitor comprises a short-chain fatty acid or salt thereof. In some embodiments, the HDAC inhibitor comprises a hydroxamic acid. In some embodiments, the HDAC inhibitor comprises a hydroxamic acid, for example, Trichostatin A, suberanilohydroxamic acid (SAHA), belinostat (PXD101), panabiostat, givinostat, resminostat, abexinostat, quisinostat, rocilinostat, practinostat, and CHR-3996. In some embodiments, the HDAC inhibitor comprises a short-chain fatty acid or salt thereof, for example, valproate, propionate, butyrate, 2,2-dimethylbutyrate, 2-ethyl-butyrate, pentanoate, hexanoate, hetanoate, octanoate, phenylbutyrate, and a salt thereof. Steliou et al., BioResearch Open Access, Vol. 1, Issue 4, doi.org/10.1089/biores.2012.0223 (2012). In some embodiments, the HDAC inhibitor comprises valproate or a salt thereof (e.g., sodium valproate). In some embodiments, the HDAC inhibitor comprises butyrate or a salt thereof (e.g., sodium butyrate). In some embodiments, the HDAC inhibitor comprises propionate or a salt thereof (e.g., sodium propionate). In some embodiments, the HDAC inhibitor comprises a benzamide, for example, entinostat, tacedinaline, 4SC202, and mocetinostat. In some embodiments, the HDAC inhibitor comprises a cyclic tetrapeptide, for example, romidepsin. In some embodiments, the HDAC inhibitor comprises a sirtuin inhibitor, for example, nicotinamide, sirtinol, cambinol, and EX-527. In some embodiment, the HDAC inhibitor comprises, [4-(2-amino-phenylcarbamoyl)-benzyl]carbamic acid pyridine-3-ylmethylester and its derivatives, pyroxamide, oxamflatin, apicidin, depsipeptide, depudecin, trapoxin, M344, scriptaid, MC 1293, sodium 1-naphtoate, CAY10398, sodium-phenylbutyrate, suberoyl bis-hydroxamic acid (SBHA), CAY10433, oxamflatin, or HC toxin. In some embodiments, the HDAC inhibitor does not comprise pyruvate or a salt thereof. In some embodiments, the HDAC inhibitor does not comprise nicotinamide. In some embodiments, the HDAC inhibitor comprises a combination of two or more HDAC inhibitors.

In some embodiments, a method disclosed herein comprises adding to the cell culture an HDAC inhibitor to a final concentration between about 0.1 mM and about 20 mM. In some embodiments, a method disclosed herein comprises culturing a cell capable of producing rAAV in a medium comprising between about 0.1 mM and about 20 mM HDAC inhibitor. In some embodiments, a cell culture disclosed herein comprises between about 0.1 mM and about 20 mM HDAC inhibitor. It is understood that a cell culture comprising, for example, 2 mM HDAC inhibitor comprises cells and a medium comprising 2 mM HDAC inhibitor. In some embodiments, the concentration of the HDAC inhibitor is between about 0.5 mM and about 10 mM. In some embodiments, the concentration of the HDAC inhibitor is between about 0.5 mM and about 5 mM. In some embodiments, the concentration of the HDAC inhibitor is between about 0.5 mM and about 3 mM. In some embodiments, the concentration of the HDAC inhibitor is about 0.5 mM, about 1 mM, about 1.5 mM, about 2 mM, about 2.5 mM, about 3 mM, about 3.5 mM, about 4 mM, about 4.5 mM, or about 5 mM. In some embodiments, the concentration of the HDAC inhibitor is about 1.5 mM, In some embodiments, the concentration of the HDAC inhibitor is about 2 mM, In some embodiments, the concentration of the HDAC inhibitor is about 3 mM, In some embodiments, the concentration of the HDAC inhibitor is about 4 mM, In some embodiments, the cell culture comprises between about 0.5 mM and about 10 mM valproate or a salt thereof (e.g., sodium valproate). In some embodiments, the cell culture comprises between about 0.5 mM and about 5 mM valproate or a salt thereof (e.g., sodium valproate). In some embodiments, the cell culture comprises between about 0.5 mM and about 3 mM valproate or a salt thereof (e.g., sodium valproate). In some embodiments, the cell culture comprises about 0.5 mM, about 1 mM, about 1.5 mM, about 2 mM, about 2.5 mM, about 3 mM, about 3.5 mM, about 4 mM, about 4.5 mM, or about 5 mM valproate or a salt thereof (e.g., sodium valproate). In some embodiments, the cell culture comprises about 1.5 mM valproate or a salt thereof (e.g., sodium valproate). In some embodiments, the cell culture comprises about 2 mM valproate or a salt thereof (e.g., sodium valproate). In some embodiments, the cell culture comprises about 3 mM valproate or a salt thereof (e.g., sodium valproate). In some embodiments, the cell culture comprises about 4 mM valproate or a salt thereof (e.g., sodium valproate).

In some embodiments, the cell culture comprises between about 0.5 mM and about 10 mM butyrate or a salt thereof (e.g., sodium butyrate). In some embodiments, the cell culture comprises between about 0.5 mM and about 5 mM butyrate or a salt thereof (e.g., sodium butyrate). In some embodiments, the cell culture comprises between about 0.5 mM and about 3 mM butyrate or a salt thereof (e.g., sodium butyrate). In some embodiments, the cell culture comprises about 0.5 mM, about 1 mM, about 1.5 mM, about 2 mM, about 2.5 mM, about 3 mM, about 3.5 mM, about 4 mM, about 4.5 mM, or about 5 mM butyrate or a salt thereof (e.g., sodium butyrate). In some embodiments, the cell culture comprises about 1.5 mM butyrate or a salt thereof (e.g., sodium butyrate). In some embodiments, the cell culture comprises about 2 mM butyrate or a salt thereof (e.g., sodium butyrate). In some embodiments, the cell culture comprises about 3 mM butyrate or a salt thereof (e.g., sodium butyrate). In some embodiments, the cell culture comprises about 4 mM butyrate or a salt thereof (e.g., sodium butyrate).

In some embodiments, the cell culture comprises between about 0.5 mM and about 10 mM propionate or a salt thereof (e.g., sodium propionate). In some embodiments, the cell culture comprises between about 0.5 mM and about 5 mM propionate or a salt thereof (e.g., sodium propionate). In some embodiments, the cell culture comprises between about 0.5 mM and about 3 mM propionate or a salt thereof (e.g., sodium propionate). In some embodiments, the cell culture comprises about 0.5 mM, about 1 mM, about 1.5 mM, about 2 mM, about 2.5 mM, about 3 mM, about 3.5 mM, about 4 mM, about 4.5 mM, or about 5 mM propionate or a salt thereof (e.g., sodium propionate). In some embodiments, the cell culture comprises about 1.5 mM propionate or a salt thereof (e.g., sodium propionate). In some embodiments, the cell culture comprises about 2 mM propionate or a salt thereof (e.g., sodium propionate). In some embodiments, the cell culture comprises about 3 mM propionate or a salt thereof (e.g., sodium propionate). In some embodiments, the cell culture comprises about 4 mM propionate or a salt thereof (e.g., sodium propionate).

In some embodiments, a method disclosed herein comprises providing a cell culture comprising a cell, introducing into the cell one or more polynucleotides and adding to the cell culture an HDAC inhibitor. In some embodiments, the HDAC inhibitor is added before introducing into the cell one or more polynucleotides. In some embodiments, the HDAC inhibitor is added after introducing into the cell one or more polynucleotides. In some embodiments, the HDAC inhibitor is added between about 1 hour and about 48 hours or between about 12 hours and about 36 hours after introducing into the cell one or more polynucleotides. In some embodiments, the HDAC inhibitor is added between about 16 hours and about 30 hours after introducing into the cell one or more polynucleotides. In some embodiments, the HDAC inhibitor is added between about 18 hours and about 26 hours after introducing into the cell one or more polynucleotides. In some embodiments, the HDAC inhibitor is added between about 18 hours and about 22 hours after introducing into the cell one or more polynucleotides. In some embodiments, the HDAC inhibitor is added between about 22 hours and about 26 hours after introducing into the cell one or more polynucleotides. In some embodiments, the HDAC inhibitor is added less than about 48 hours or less than about 36 hours after introducing into the cell one or more polynucleotides. In some embodiments, the HDAC inhibitor is added at least about 6 hours, at least about 9 hours, at least about 12 hours, at least about 18 hours, at least about 20 hours after introducing into the cell one or more polynucleotides. In some embodiments, the HDAC inhibitor is added about 6 hours, about 9 hours, about 12 hours, about 18 hours, about 20 hours, about 22 hours, about 24 hours, about 30 hours, about 36 hours, or about 48 hours after introducing into the cell one or more polynucleotides. In some embodiments, the HDAC inhibitor is added about 18 hours after introducing into the cell one or more polynucleotides. In some embodiments, the HDAC inhibitor is added about 20 hours after introducing into the cell one or more polynucleotides. In some embodiments, the HDAC inhibitor is added about 22 hours after introducing into the cell one or more polynucleotides. In some embodiments, the HDAC inhibitor is added about 24 hours after introducing into the cell one or more polynucleotides. In some embodiments, the introducing into the cell one or more polynucleotides comprises transfecting the cell with one or more polynucleotides.

In some embodiments, the cell culture medium is replaced between introducing into the cell one or more polynucleotides and adding to the cell culture an HDAC inhibitor. In some embodiments, the cell culture medium is supplemented between introducing into the cell one or more polynucleotides and adding to the cell culture an HDAC inhibitor. In some embodiments, the cell culture medium is supplemented with one or more of nutrients, salts, buffering agents, and additives (e.g., antifoam agent) between introducing into the cell one or more polynucleotides and adding to the cell culture an HDAC inhibitor. In some embodiments, the introducing into the cell one or more polynucleotides comprises transfecting the cell with one or more polynucleotides.

In some embodiments, a method disclosed herein comprises adding to a cell culture a sodium salt. In some embodiments, a method disclosed herein comprises culturing a cell in a medium comprising a sodium salt. In some embodiments, a cell culture disclosed herein comprises a sodium salt. It is understood that a cell culture comprising a sodium salt comprises cells and a medium comprising the sodium salt.

In some embodiment, a sodium salt is an inorganic salt. In some embodiments, the sodium salt is an organic salt. In some embodiments, the sodium salt is a sodium halide comprising a halogen (e.g., fluorine, chlorine, bromine, and iodine). In some embodiments, the sodium salt is sodium chloride or sodium bromide. In some embodiments, the sodium salt is sodium chloride, sodium carbonate, sodium phosphate, or sodium sulfate. In some embodiments, the sodium salt is sodium chloride.

In some embodiments, a cell culture or a cell culture medium comprises between about 120 mM and about 250 mM of the sodium salt. In some embodiments, the cell culture or cell culture medium comprises between about 130 mM and about 160 mM, between about 150 mM and about 190 mM, or between about 180 mM and about 240 mM of the sodium salt. In some embodiments, the cell culture or a cell culture medium comprises between about 150 mM and about 240 mM of the sodium salt. In some embodiments, the cell culture or a cell culture medium comprises between about 150 mM and about 190 mM of the sodium salt. In some embodiments, the cell culture or a cell culture medium comprises between about 180 mM and about 240 mM of the sodium salt. In some embodiments, the sodium salt is sodium chloride.

In some embodiments, a cell culture or a cell culture medium comprises between about 120 mM and about 250 mM of sodium chloride. In some embodiments, the cell culture or cell culture medium comprises between about 130 mM and about 160 mM, between about 150 mM and about 190 mM, or between about 180 mM and about 240 mM of sodium chloride. In some embodiments, the cell culture or a cell culture medium comprises between about 150 mM and about 240 mM of sodium chloride. In some embodiments, the cell culture or a cell culture medium comprises between about 150 mM and about 190 mM of sodium chloride. In some embodiments, the cell culture or a cell culture medium comprises between about 180 mM and about 240 mM of sodium chloride. In some embodiments, the sodium salt is sodium chloride. In some embodiments, the final concentration of the sodium salt is increased to about 140 mM sodium chloride. In some embodiments, the final concentration of the sodium salt is increased to about 170 mM sodium chloride. In some embodiments, the final concentration of the sodium salt is increased to about 200 mM sodium chloride.

In some embodiments, a method disclosed herein comprises adding to a cell culture sufficient amount of a sodium salt to increase the final concentration of the sodium salt by between about 20 mM and about 150 mM. In some embodiments, the final concentration of the sodium salt is increased by between about 20 mM and about 50 mM. In some embodiments, the final concentration of the sodium salt is increased by between about 40 mM and about 80 mM. In some embodiments, the final concentration of the sodium salt is increased by between about 70 mM and about 120 mM. In some embodiments, the final concentration of the sodium salt is increased by between about 40 mM and about 140 mM. In some embodiments, the final concentration of the sodium salt is increased by about 30 mM. In some embodiments, the final concentration of the sodium salt is increased by about 60 mM. In some embodiments, the final concentration of the sodium salt is increased by about 90 mM. In some embodiments, the sodium salt is sodium chloride.

In some embodiments, a method disclosed herein comprises adding to a cell culture sufficient amount of a sodium chloride to increase the final concentration of the sodium chloride by between about 20 mM and about 150 mM. In some embodiments, the final concentration of the sodium chloride is increased by between about 20 mM and about 50 mM. In some embodiments, the final concentration of the sodium chloride is increased by between about 40 mM and about 80 mM. In some embodiments, the final concentration of the sodium chloride is increased by between about 70 mM and about 120 mM. In some embodiments, the final concentration of the sodium chloride is increased by between about 40 mM and about 140 mM. In some embodiments, the final concentration of the sodium chloride is increased by about 30 mM. In some embodiments, the final concentration of the sodium chloride is increased by about 60 mM. In some embodiments, the final concentration of the sodium chloride is increased by about 90 mM.

In some embodiments, the cell culture comprises the sodium salt before adding the sodium salt to further increase its concentration by, for example, 90 mM. In some embodiments, the cell culture comprises about 90 mM, about 100 mM, or about 110 mM of the sodium salt before it is added to the cell culture to further increase its concentration. It is understood that when a cell culture comprises about 110 mM sodium chloride, and a sufficient amount of sodium chloride is added to the cell culture to increase its concentration by about 90 mM, the final concentration of the sodium chloride will be about 200 mM. In some embodiments, the sodium salt is sodium chloride.

In some embodiments, the cell culture comprises about 90 mM, about 100 mM, or about 110 mM of sodium chloride before it is added to the cell culture to further increase its concentration.

In some embodiments, a method disclosed herein comprises adding to a cell culture sufficient amount of a sodium salt to increase the final concentration of the sodium salt to between about 120 mM and about 250 mM. In some embodiments, the final concentration of the sodium salt is increased to between about 130 mM and about 160 mM. In some embodiments, the final concentration of the sodium salt is increased to between about 150 mM and about 190 mM. In some embodiments, the final concentration of the sodium salt is increased to between about 180 mM and about 240 mM. In some embodiments, the final concentration of the sodium salt is increased to between about 150 mM and about 240 mM. In some embodiments, the final concentration of the sodium salt is increased to about 140 mM. In some embodiments, the final concentration of the sodium salt is increased to about 170 mM. In some embodiments, the final concentration of the sodium salt is increased to about 200 mM. In some embodiments, the sodium salt is sodium chloride.

In some embodiments, a method disclosed herein comprises adding to a cell culture sufficient amount of a sodium chloride to increase the final concentration of the sodium chloride to between about 120 mM and about 250 mM. In some embodiments, the final concentration of the sodium chloride is increased to between about 130 mM and about 160 mM. In some embodiments, the final concentration of the sodium chloride is increased to between about 150 mM and about 190 mM. In some embodiments, the final concentration of the sodium chloride is increased to between about 180 mM and about 240 mM. In some embodiments, the final concentration of the sodium chloride is increased to between about 150 mM and about 240 mM. In some embodiments, the final concentration of the sodium chloride is increased to about 140 mM. In some embodiments, the final concentration of the sodium chloride is increased to about 170 mM. In some embodiments, the final concentration of the sodium chloride is increased to about 200 mM.

In some embodiments, a method disclosed herein comprises (a) providing a cell culture comprising a cell, (b) introducing into the cell one or more polynucleotides, (c) adding to the cell culture an HDAC inhibitor, and (d) adding to the cell culture a sodium salt (e.g., sodium chloride). It is to be understood that (b), (c) and (d) can be performed in any order. In some embodiments, (b), (c) and (d) are performed in the order of (b)-(c)-(d). In some embodiments, (b), (c) and (d) are performed in the order of (b)-(d)-(c). In some embodiments, (b), (c) and (d) are performed in the order of (d)-(c)-(b). In some embodiments, (b), (c) and (d) are performed in the order of (d)-(b)-(c). In some embodiments, (c) and (d) are performed simultaneously after (b). In some embodiments, (c) and (d) are performed simultaneously by adding to the cell culture a composition comprising the HDAC inhibitor and the sodium salt (e.g., sodium chloride). In some embodiments, (c) and (d) are performed simultaneously by adding to the cell culture a first composition comprising the HDAC inhibitor and a second composition comprising the sodium salt (e.g., sodium chloride). In some embodiments, the introducing into the cell one or more polynucleotides comprises transfecting the cell with one or more polynucleotides.

In some embodiments, a method disclosed herein comprises (a) providing a cell culture comprising a cell, (b) introducing into the cell one or more polynucleotides, (c)

adding to the cell culture an HDAC inhibitor, and (d) adding to the cell culture a sodium salt (e.g., sodium chloride), wherein (c) is performed after (b). In some embodiments, (c) is performed between about 1 hour and about 48 hours or between about 12 hours and about 36 hours after (b). In some embodiments, (c) is performed less than about 48 hours or less than about 36 hours after (b). In some embodiments, (c) is performed at least about 6 hours, at least about 9 hours, at least about 12 hours, or at least about 18 hours after (b). In some embodiments, (c) is performed about 6 hours, about 9 hours, about 12 hours, about 18 hours, about 20 hours, about 22 hours, about 24 hours, about 30 hours, about 36 hours, or about 48 hours after (b). In some embodiments, (c) is performed about 24 hours after (b). In some embodiments, (c) is performed about 20 hours after (b). In some embodiments, the introducing into the cell one or more polynucleotides comprises transfecting the cell with one or more polynucleotides.

In some embodiments, a method disclosed herein comprises (a) providing a cell culture comprising a cell, (b) introducing into the cell one or more polynucleotides, (c) adding to the cell culture an HDAC inhibitor, and (d) adding to the cell culture a sodium salt (e.g., sodium chloride), wherein (b), (c) and (d) are performed in the order of (b)-(c)-(d). In some embodiments, (d) is performed between about 5 minutes and about 6 hours after (c). In some embodiments, (d) is performed between about 20 minutes and about 2 hours after (c). In some embodiments, (d) is performed less than about 2 hours or less than about 1 hour after (c). In some embodiments, (d) is performed at least about 5 minutes, at least about 10 minutes hours, at least about 20 minutes, at least about 30 minutes, at least about 40 minutes, at least about 50 minutes after (c). In some embodiments, (d) is performed at least about 30 minutes after (c). In some embodiments, (d) is performed about 10 minutes, about 20 minutes, about 30 minutes, about 40 minutes, about 50 minutes, or about 60 minutes after (c). In some embodiments, (d) is performed about 40 minutes after (c). In some embodiments, the introducing into the cell one or more polynucleotides comprises transfecting the cell with one or more polynucleotides.

In some embodiments, a method disclosed herein comprises (a) providing a cell culture comprising a cell, (b) introducing into the cell one or more polynucleotides, (c) adding to the cell culture an HDAC inhibitor, and (d) adding to the cell culture a sodium salt (e.g., sodium chloride), wherein (b), (c) and (d) are performed in the order of (b)-(c)-(d). In some embodiments, (c) is performed between about 1 hour and about 48 hours or between about 12 hours and about 36 hours after (b). In some embodiments, (c) is performed less than about 48 hours or less than about 36 hours after (b). In some embodiments, (c) is performed at least about 6 hours, at least about 9 hours, at least about 12 hours, or at least about 18 hours after (b). In some embodiments, (c) is performed about 6 hours, about 9 hours, about 12 hours, about 18 hours, about 20 hours, about 22 hours, about 24 hours, about 30 hours, about 36 hours, or about 48 hours after (b). In some embodiments, (c) is performed about 24 hours after (b). In some embodiments, (c) is performed about 20 hours after (b). In some embodiments, (d) is performed between about 5 minutes and about 6 hours after (c). In some embodiments, (d) is performed between about 20 minutes and about 2 hours after (c). In some embodiments, (d) is performed less than about 2 hours or less than about 1 hour after (c). In some embodiments, (d) is performed at least about 5 minutes, at least about 10 minutes hours, at least about 20 minutes, at least about 30 minutes, at least about 40 minutes, at least about 50 minutes after (c). In some embodiments, (d) is performed at least about 30 minutes after (c). In some embodiments, (d) is performed about 10 minutes, about 20 minutes, about 30 minutes, about 40 minutes, about 50 minutes, or about 60 minutes after (c). In some embodiments, (d) is performed about 40 minutes after (c).

In some embodiments, a method disclosed herein comprises providing a cell culture comprising a cell, introducing into the cell one or more polynucleotides, adding to the cell culture an HDAC inhibitor, adding to the cell culture a sodium salt (e.g., sodium chloride), and maintaining the cell culture under conditions that allow production of the rAAV particles. In some embodiments, the cell culture is maintained for between about 2 days and about 10 days after introducing into the cell one or more polynucleotides. In some embodiments, the cell culture is maintained for between about 5 days and about 14 days or more after introducing into the cell one or more polynucleotides. In some embodiments, the cell culture is maintained for between about 2 days and about 7 days after introducing into the cell one or more polynucleotides. In some embodiments, the cell culture is maintained for about 2 days, about 3 days, about 4 days, about 5 days, about 6 days, or about 7 days after introducing into the cell one or more polynucleotides. In some embodiments, the cell culture is maintained for about 5 days after introducing into the cell one or more polynucleotides. In some embodiments, the cell culture is maintained for about 6 days after introducing into the cell one or more polynucleotides. In some embodiments, the cell culture is maintained under conditions that allow production of the rAAV particles for continuous harvest. In some embodiments, the introducing into the cell one or more polynucleotides comprises transfecting the cell with one or more polynucleotides.

In some embodiments, a method disclosed herein increases production of rAAV particles relative to a method that does not comprise adding an HDAC inhibitor or adding a sodium salt to the cell culture. In some embodiments, a method disclosed herein increases rAAV production by at least about 50%, at least about 75%, or at least about 100%. In some embodiments, a method disclosed herein increases rAAV production by at least about two-fold, at least about three-fold, or at least about five-fold. In some embodiments, a method disclosed herein increases rAAV production by at least about two-fold. In some embodiments, the increase in production is determined by comparing the rAAV titer in the production culture. In some embodiments, rAAV titer is measured as genome copy (GC) per milliliter of the production culture. In some embodiments, the rAAV particles comprise a capsid protein from an AAV capsid serotype selected from AAV8 and AAV9. In some embodiments, the rAAV particles have an AAV capsid serotype of AAV8. In some embodiments, the rAAV particles have an AAV capsid serotype of AAV9. In some embodiments, the rAAV particles have a capsid serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles have a capsid protein with high sequence homology to AAV8 or AAV9 such as, AAV.rh10, AAV.rh20, AAV.rh39, AAV.Rh74, AAV.RHM4-1, and AAV.hu37.

In some embodiments, a method disclosed herein increases production of rAAV particles while maintaining or improving the quality attributes of the rAAV particles and compositions comprising thereof. In some embodiments, the quality of rAAV particles and compositions comprising thereof is assessed by determining the concentration of rAAV particles (e.g., GC/ml), the percentage of particles comprising a copy of the rAAV genome; the ratio of particles without a genome, infectivity of the rAAV particles, stability of rAAV particles, concentration of residual host cell proteins, or concentration of residual host cell nucleic acids (e.g., host cell genomic DNA, plasmid encoding rep and cap genes, plasmid encoding helper functions, plasmid encoding rAAV genome). In some embodiments, the quality of rAAV particles produced by a method disclosed herein or compositions comprising thereof is the same as that of rAAV particles or compositions produced by a method that does not comprise adding an HDAC inhibitor or adding a sodium salt to the cell culture. In some embodiments, the quality of rAAV particles produced by a method disclosed herein or compositions comprising thereof is better than the quality of rAAV particles or compositions produced by a method that does not comprise adding an HDAC inhibitor or adding a sodium salt to the cell culture.

In some embodiments, a method disclosed herein produces between about $1\times10e+10$ GC/ml and about $1\times10e+13$ GC/ml rAAV particles. In some embodiments, a method disclosed herein produces between about $1\times10e+10$ GC/ml and about $1\times10e+11$ GC/ml rAAV particles. In some embodiments, a method disclosed herein produces between about $5\times10e+10$ GC/ml and about $1\times10e+12$ GC/ml rAAV particles. In some embodiments, a method disclosed herein produces between about $5\times10e+10$ GC/ml and about $1\times10e+13$ GC/ml rAAV particles. In some embodiments, a method disclosed herein produces between about $1\times10e+11$ GC/ml and about $1\times10e+13$ GC/ml rAAV particles. In some embodiments, a method disclosed herein produces between about $5\times10e+10$ GC/ml and about $5\times10e+12$ GC/ml rAAV particles. In some embodiments, a method disclosed herein produces between about $1\times10e+11$ GC/ml and about $5\times10e+12$ GC/ml rAAV particles. In some embodiments, a method disclosed herein produces more than about $1\times10e+11$ GC/ml rAAV particles. In some embodiments, a method disclosed herein produces more than about $5\times10e+11$ GC/ml rAAV particles. In some embodiments, a method disclosed herein produces more than about $1\times10e+12$ GC/ml rAAV particles. In some embodiments, the rAAV particles comprise a capsid protein from an AAV capsid serotype selected from AAV8 and AAV9. In some embodiments, the rAAV particles have an AAV capsid serotype of AAV8. In some embodiments, the rAAV particles have an AAV capsid serotype of AAV9. In some embodiments, the rAAV particles comprise a capsid protein from an AAV capsid serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles comprise a capsid protein with high sequence homology to AAV8 or AAV9 such as, AAV.rh10, AAV.rh20, AAV.rh39, AAV.Rh74, AAV.RHM4-1, and AAV.hu37.

In some embodiments, a method disclosed herein produces at least about $5\times10e+10$ GC/ml rAAV particles. In some embodiments, a method disclosed herein produces at least about $1\times10e+11$ GC/ml rAAV particles. In some embodiments, a method disclosed herein produces at least about $5\times10e+11$ GC/ml rAAV particles. In some embodiments, a method disclosed herein produces at least about $1\times10e+12$ GC/ml rAAV particles. In some embodiments, a method disclosed herein produces at least about $5\times10e+12$ GC/ml rAAV particles. In some embodiments, a method disclosed herein produces at least about $1\times10e+13$ GC/ml rAAV particles. In some embodiments, a method disclosed herein produces at least about $5\times10e+13$ GC/ml rAAV particles. In some embodiments, the rAAV particles comprise a capsid protein from an AAV capsid serotype selected from AAV8 and AAV9. In some embodiments, the rAAV particles have an AAV capsid serotype of AAV8. In some embodiments, the rAAV particles have an AAV capsid serotype of AAV9. In some embodiments, the rAAV particles comprise a capsid protein from an AAV capsid serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles comprise a capsid protein with high sequence homology to AAV8 or AAV9 such as, AAV.rh10, AAV.rh20, AAV.rh39, AAV.Rh74, AAV.RHM4-1, and AAV.hu37.

Numerous cell culture based systems are known in the art for production of rAAV particles, any of which can be used to practice a method disclosed herein. The cell culture based systems include transfection, stable cell line production, and infectious hybrid virus production systems which include Adenovirus-AAV hybrids, herpesvirus-AAV hybrids and baculovirus-AAV hybrids. rAAV production cultures for the production of rAAV virus particles all require; (1) suitable host cells, including, for example, human-derived cell lines such as HeLa, A549, or HEK293 cells and their derivatives (HEK293T cells, HEK293F cells), mammalian cell lines such as Vero, CHO cells or CHO-derived cells, or insect-derived cell lines such as SF-9 in the case of baculovirus production systems; (2) suitable helper virus function, provided by wild type or mutant adenovirus (such as temperature sensitive adenovirus), herpes virus, baculovirus, or a plasmid construct providing helper functions; (3) AAV rep and cap genes and gene products; (4) a transgene (such as a therapeutic transgene) flanked by AAV ITR sequences; and (5) suitable media and media components to support rAAV production.

In one aspect, provided herein is a method of producing rAAV particles, comprising (a) providing a cell culture comprising an insect cell; (b) introducing into the cell one or more baculovirus vectors encoding at least one of: i. an rAAV genome to be packaged, ii. an AAV rep protein sufficient for packaging, and iii. an AAV cap protein sufficient for packaging; (c) adding to the cell culture an HDAC inhibitor to a final concentration between about 0.1 mM and about 20 mM; and maintaining the cell culture under conditions that allow production of the rAAV particles for between about 2 days and about 15 days or longer after (b). In some embodiments, the method comprises using a first baculovirus vector encoding the rep and cap genes and a second baculovirus vector encoding the rAAV genome. In some embodiments, the method comprises using a baculovirus encoding the rAAV genome and an insect cell expressing the rep and cap genes. In some embodiments, the method comprises using a baculovirus vector encoding the rep and cap genes and the rAAV genome. In some embodiments, the insect cell is an Sf-9 cell. In some embodiments, the insect cell is an Sf-9 cell comprising one or more stably integrated heterologous polynucleotide encoding the rep and cap genes. In some embodiments, the method further comprises adding to the culture a sodium salt in sufficient amount to increase the final concentration of the sodium salt by between about 20 mM and about 150 mM. In some embodiments, the HDAC inhibitor is valproate, propionate, butyrate, or a salt thereof.

In some embodiments, a method disclosed herein uses a baculovirus production system. In some embodiments the baculovirus production system uses a first baculovirus encoding the rep and cap genes and a second baculovirus encoding the rAAV genome. In some embodiments the baculovirus production system uses a baculovirus encoding the rAAV genome and a host cell expressing the rep and cap genes. In some embodiments the baculovirus production system uses a baculovirus encoding the rep and cap genes and the rAAV genome. In some embodiments, the baculovirus production system uses Sf-9 cells.

A skilled artisan is aware of the numerous methods by which AAV rep and cap genes, AAV helper genes (e.g., adenovirus E1a gene, E1b gene, E4 gene, E2a gene, and VA gene), and rAAV genomes (comprising one or more genes of interest flanked by inverted terminal repeats (ITRs)) can be introduced into cells to produce or package rAAV. The phrase "adenovirus helper functions" refers to a number of viral helper genes expressed in a cell (as RNA or protein) such that the AAV grows efficiently in the cell. The skilled artisan understands that helper viruses, including adenovirus and herpes simplex virus (HSV), promote AAV replication and certain genes have been identified that provide the essential functions, e.g. the helper may induce changes to the cellular environment that facilitate such AAV gene expression and replication. In some embodiments of a method disclosed herein, AAV rep and cap genes, helper genes, and rAAV genomes are introduced into cells by transfection of one or more plasmid vectors encoding the AAV rep and cap genes, helper genes, and rAAV genome. In some embodiments of a method disclosed herein, AAV rep and cap genes, helper genes, and rAAV genomes can be introduced into cells by transduction with viral vectors, for example, rHSV vectors encoding the AAV rep and cap genes, helper genes, and rAAV genome. In some embodiments of a method disclosed herein, one or more of AAV rep and cap genes, helper genes, and rAAV genomes are introduced into the cells by transduction with an rHSV vector. In some embodiments, the rHSV vector encodes the AAV rep and cap genes. In some embodiments, the rHSV vector encodes the helper genes. In some embodiments, the rHSV vector encodes the rAAV genome. In some embodiments, the rHSV vector encodes the AAV rep and cap genes. In some embodiments, the rHSV vector encodes the helper genes and the rAAV genome. In some embodiments, the rHSV vector encodes the helper genes and the AAV rep and cap genes.

In one aspect, provided herein is a method of producing rAAV particles, comprising (a) providing a cell culture comprising a cell; (b) introducing into the cell one or more rHSV vectors encoding at least one of: i. an rAAV genome to be packaged, ii. helper functions necessary for packaging the rAAV particles, iii. an AAV rep protein sufficient for packaging, and iv. an AAV cap protein sufficient for packaging; (c) adding to the cell culture an HDAC inhibitor to a final concentration between about 0.1 mM and about 20 mM; and maintaining the cell culture under conditions that allow production of the rAAV particles for between about 2 days and about 15 days or longer after (b). In some embodiments, the rHSV vector encodes the AAV rep and cap genes. In some embodiments, the rHSV vector encodes helper functions. In some embodiments, the rHSV vector comprises one or more endogenous genes that encode helper functions. In some embodiments, the rHSV vector comprises one or more heterogeneous genes that encode helper functions. In some embodiments, the rHSV vector encodes the rAAV genome. In some embodiments, the rHSV vector encodes the AAV rep and cap genes. In some embodiments, the rHSV vector encodes helper functions and the rAAV genome. In some embodiments, the rHSV vector encodes helper functions and the AAV rep and cap genes. In some embodiments, the cell comprises one or more stably integrated heterologous polynucleotide encoding the rep and cap genes. In some embodiments, the method further comprises adding to the culture a sodium salt in sufficient amount to increase the final concentration of the sodium salt by between about 20 mM and about 150 mM. In some embodiments, the HDAC inhibitor is valproate, propionate, butyrate, or a salt thereof.

In one aspect, provided herein is a method of producing rAAV particles, comprising (a) providing a cell culture comprising a mammalian cell; (b) introducing into the cell one or more polynucleotides encoding at least one of: i. an rAAV genome to be packaged, ii. helper functions necessary for packaging the rAAV particles, iii. an AAV rep protein sufficient for packaging, and iv. an AAV cap protein sufficient for packaging; (c) adding to the cell culture an HDAC inhibitor to a final concentration between about 0.1 mM and about 20 mM; and maintaining the cell culture under conditions that allow production of the rAAV particles for between about 2 days and about 15 days or longer after (b). In some embodiments, the helper functions are encoded by adenovirus genes. In some embodiments, the mammalian cell comprises one or more stably integrated heterologous polynucleotide encoding the rep and cap genes. In some embodiments, the method further comprises adding to the culture a sodium salt in sufficient amount to increase the final concentration of the sodium salt by between about 20 mM and about 150 mM. In some embodiments, the HDAC inhibitor is valproate, propionate, butyrate, or a salt thereof.

Molecular biology techniques to develop plasmid or viral vectors encoding the AAV rep and cap genes, helper genes, and/or rAAV genome are commonly known in the art. In some embodiments, AAV rep and cap genes are encoded by one plasmid vector. In some embodiments, AAV helper genes (e.g., adenovirus E1a gene, E1b gene, E4 gene, E2a gene, and VA gene) are encoded by one plasmid vector. In some embodiments, the E1a gene or E1b gene is stably expressed by the host cell, and the remaining AAV helper genes are introduced into the cell by transfection by one viral vector. In some embodiments, the E1a gene and E1b gene are stably expressed by the host cell, and the E4 gene, E2a gene, and VA gene are introduced into the cell by transfection by one plasmid vector. In some embodiments, one or more helper genes are stably expressed by the host cell, and one or more helper genes are introduced into the cell by transfection by one plasmid vector. In some embodiments, the helper genes are stably expressed by the host cell. In some embodiments, AAV rep and cap genes are encoded by one viral vector. In some embodiments, AAV helper genes (e.g., adenovirus E1a gene, E1b gene, E4 gene, E2a gene, and VA gene) are encoded by one viral vector. In some embodiments, the E1a gene or E1b gene is stably expressed by the host cell, and the remaining AAV helper genes are introduced into the cell by transfection by one viral vector. In some embodiments, the E1a gene and E1b gene are stably expressed by the host cell, and the E4 gene, E2a gene, and VA gene are introduced into the cell by transfection by one viral vector. In some embodiments, one or more helper genes are stably expressed by the host cell, and one or more helper genes are introduced into the cell by transfection by one viral vector. In some embodiments, the AAV rep and cap genes, the adenovirus helper functions necessary for packaging, and the rAAV genome to be packaged are introduced to the cells by transfection with one or more polynucleotides, e.g., vectors. In some embodiments, a method disclosed herein comprises transfecting the cells with a mixture of three polynucleotides: one encoding the cap and rep genes, one encoding adenovirus helper functions necessary for packaging (e.g., adenovirus E1a gene, E1b gene, E4 gene, E2a gene, and VA gene), and one encoding the rAAV genome to be packaged. In some embodiments, the AAV cap gene is an AAV8 or AAV9 cap gene. In some embodiments, the AAV cap gene is an AAV.rh8, AAV.rh10, AAV.rh20, AAV.rh39, AAV.Rh74, AAV.RHM4-1, AAV.hu37, AAV.PHB, or AAV.7m8 cap gene. In some embodiments, the AAV cap gene encodes a capsid protein with high sequence homology to AAV8 or AAV9 such as, AAV.rh10, AAV.rh20, AAV.rh39, AAV.Rh74, AAV.RHM4-1, and AAV.hu37. In some embodiments, the vector encoding the rAAV genome to be packaged comprises a gene of interest flanked by AAV ITRs. In some embodiments, the AAV ITRs are from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other AAV serotype.

Any combination of vectors can be used to introduce AAV rep and cap genes, AAV helper genes, and rAAV genome to a cell in which rAAV particles are to be produced or packaged. In some embodiments of a method disclosed herein, a first plasmid vector encoding an rAAV genome comprising a gene of interest flanked by AAV inverted terminal repeats (ITRs), a second vector encoding AAV rep and cap genes, and a third vector encoding helper genes can be used. In some embodiments, a mixture of the three vectors is co-transfected into a cell.

In some embodiments, a combination of transfection and infection is used by using both plasmid vectors as well as viral vectors.

In some embodiments, one or more of rep and cap genes, and AAV helper genes are constitutively expressed by the cells and does not need to be transfected or transduced into the cells. In some embodiments, the cell constitutively expresses rep and/or cap genes. In some embodiments, the cell constitutively expresses one or more AAV helper genes. In some embodiments, the cell constitutively expresses E1a. In some embodiments, the cell comprises a stable transgene encoding the rAAV genome.

In some embodiments, AAV rep, cap, and helper genes (e.g., E1a gene, E1b gene, E4 gene, E2a gene, or VA gene) can be of any AAV serotype. Similarly, AAV ITRs can also be of any AAV serotype. For example, in some embodiments, AAV ITRs are from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other AAV serotypes (e.g., a hybrid serotype harboring sequences from more than one serotype). In some embodiments, AAV cap gene is from AAV9 or AAV8 cap gene. In some embodiments, an AAV cap gene is from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other AAV serotypes (e.g., a hybrid serotype harboring sequences from more than one serotype). In some embodiments, AAV rep and cap genes for the production of a rAAV particle is from different serotypes. For example, the rep gene is from AAV2 whereas the cap gene is from AAV9.

Any suitable method known in the art may be used for transfecting a cell may be used for the production of rAAV particles according to a method disclosed herein. In some embodiments, a method disclosed herein comprises transfecting a cell using a chemical based transfection method. In some embodiments, the chemical based transfection method uses calcium phosphate, highly branched organic compounds (dendrimers), cationic polymers (e.g., DEAE dextran or polyethylenimine (PEI)), lipofection. In some embodiments, the chemical based transfection method uses cationic polymers (e.g., DEAE dextran or polyethylenimine (PEI)). In some embodiments, the chemical based transfection method uses polyethylenimine (PEI). In some embodiments, the chemical based transfection method uses DEAE dextran. In some embodiments, the chemical based transfection method uses calcium phosphate.

Any suitable media known in the art may be used for the production of rAAV particles according to a method disclosed herein. These media include, without limitation, media produced by Hyclone Laboratories and JRH including Modified Eagle Medium (MEM), Dulbecco's Modified Eagle Medium (DMEM), and Sf-900 II SFM media as described in U.S. Pat. No. 6,723,551, which is incorporated herein by reference in its entirety. In some embodiments, the medium comprises Dynamis™ Medium, FreeStyle™ 293 Expression Medium, or Expi293™ Expression Medium from Invitrogen/ThermoFisher. In some embodiments, the medium comprises Dynamis™ Medium. In some embodiments, a method disclosed herein uses a cell culture comprising a serum-free medium, an animal-component free medium, or a chemically defined medium. In some embodiments, the medium is an animal-component free medium. In some embodiments, the medium comprises serum. In some embodiments, the medium comprises fetal bovine serum. In some embodiments, the medium is a glutamine-free medium. In some embodiments, the medium comprises glutamine. In some embodiments, the medium is supplemented with one or more of nutrients, salts, buffering agents, and additives (e.g., antifoam agent). In some embodiments, the medium is supplemented with glutamine. In some embodiments, the medium is supplemented with serum. In some embodiments, the medium is supplemented with fetal bovine serum. In some embodiments, the medium is supplemented with poloxamer, e.g., Kolliphor® P 188 Bio. In some embodiments, a medium is a base medium. In some embodiments, the medium is a feed medium.

rAAV production cultures can routinely be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, multilayer or multitray tissue culture flasks (or stacks, e.g. hyperstacks), microcarriers, and packed-bed or fluidized-bed bioreactors. rAAV vector production cultures may also include suspension-adapted host cells such as HeLa cells, HEK293 cells, HEK293 derived cells (e.g., HEK293T cells, HEK293F cells), Vero cells, CHO cells, CHO-K1 cells, CHO derived cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells and SF-9 cells which can be cultured in a variety of ways including, for example, spinner flasks, stirred tank bioreactors, and disposable systems such as the Wave bag system. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety.

Any cell or cell line that is known in the art to produce rAAV particles can be used in any one of the methods disclosed herein. In some embodiments, a method of producing rAAV particles or increasing the production of rAAV particles disclosed herein uses HeLa cells, HEK293 cells, HEK293 derived cells (e.g., HEK293T cells, HEK293F cells), Vero cells, CHO cells, CHO-K1 cells, CHO derived cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells or SF-9 cells. In some embodiments, a method disclosed herein uses mammalian cells. In some embodiments, a method disclosed herein uses insect cells, e.g., SF-9 cells. In some embodiments, a method disclosed herein uses HEK293 cells. In some embodiments, a method disclosed herein uses HEK293 cells adapted for growth in suspension culture.

In some embodiments, a cell culture disclosed herein is a suspension culture. In some embodiments, a cell culture disclosed herein is a suspension culture comprising HEK293. In some embodiments, a cell culture disclosed herein is a suspension culture comprising HEK293 cells adapted for growth in suspension culture. In some embodiments, a cell culture disclosed herein comprises a serum-free medium, an animal-component free medium, or a chemically defined medium. In some embodiments, a cell culture disclosed herein comprises a serum-free medium. In some embodiments, suspension-adapted cells are cultured in a shaker flask, a spinner flask, a cellbag, or a bioreactor.

In some embodiments, a cell culture disclosed herein comprises cells attached to a substrate (e.g., microcarriers) that are themselves in suspension in a medium. In some embodiments, the cells are HEK293 cells.

In some embodiments, a cell culture disclosed herein is an adherent culture. In some embodiments, a cell culture disclosed herein is an adherent culture comprising HEK293. In some embodiments, a cell culture disclosed herein comprises a serum-free medium, an animal-component free medium, or a chemically defined medium. In some embodiments, a cell culture disclosed herein comprises a serum-free medium.

In some embodiments, a cell culture disclosed herein comprises a high density cell culture. In some embodiments, the culture has a total cell density of between about 1×10E+06 cells/ml and about 30×10E+06 cells/ml. In some embodiments, more than about 50% of the cells are viable cells. In some embodiments, the cells are HeLa cells, HEK293 cells, HEK293 derived cells (e.g., HEK293T cells, HEK293F cells), Vero cells, or SF-9 cells. In further embodiments, the cells are HEK293 cells. In further embodiments, the cells are HEK293 cells adapted for growth in suspension culture.

Methods disclosed herein can be used in the production of rAAV particles comprising a capsid protein from any AAV capsid serotype. In some embodiments, the rAAV particles comprise a capsid protein from an AAV capsid serotype selected from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise a capsid protein that is a derivative, modification, or pseudotype of AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 capsid protein.

In some embodiments, the rAAV particles comprise a capsid protein from an AAV capsid serotype selected from AAV8 and AAV9. In some embodiments, the rAAV particles have an AAV capsid serotype of AAV8. In some embodiments, the rAAV particles have an AAV capsid serotype of AAV9.

In some embodiments, the rAAV particles comprise a capsid protein from an AAV capsid serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles comprise a capsid protein with high sequence homology to AAV8 or AAV9 such as, AAV.rh10, AAV.rh20, AAV.rh39, AAV.Rh74, AAV.RHM4-1, and AAV.hu37.

In some embodiments, the rAAV particles comprise a capsid protein that is a derivative, modification, or pseudotype of AAV8 or AAV9 capsid protein. In some embodiments, the rAAV particles comprise a capsid protein that has an AAV8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV8 capsid protein.

In some embodiments, the rAAV particles comprise a capsid protein that is a derivative, modification, or pseudotype of AAV9 capsid protein. In some embodiments, rAAV particles comprise a capsid protein that has an AAV9 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV9 capsid protein.

In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of AAV.rh8, AAV.rh10, AAV.rh20, AAV.rh39, AAV.Rh74, AAV.RHM4-1, AAV.hu37, AAV.PHB, or AAV.7m8 capsid protein. In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of an AAV capsid protein with high sequence homology to AAV8 or AAV9 such as, AAV.rh10, AAV.rh20, AAV.rh39, AAV.Rh74, AAV.RHM4-1, and AAV.hu37.

In additional embodiments, the rAAV particles comprise a mosaic capsid. In additional embodiments, the rAAV particles comprise a pseudotyped rAAV particle. In additional embodiments, the rAAV particles comprise a capsid containing a capsid protein chimera of two or more AAV capsid serotypes.

In some embodiments of the methods disclosed herein large volumes of cell culture can be present (e.g., during the commercial manufacturing processes). In some embodiments the methods disclosed herein are suitable for the processing of a large volume of cell culture comprising rAAV particles. The term "large volume" refers to volumes associated with the commercial and/or industrial production of rAAV particles. In some embodiments, the term "large volume" refers to between about 20 liters and about 20000 liters, between about 50 liters and about 20000 liters, between about 100 liters and about 20000 liters, between about 500 liters and about 20000 liters, between about 1000 liters and about 20000 liters, between about 20 liters and about 5000 liters, between about 50 liters and about 5000 liters, between about 100 liters and about 3000 liters, between about 500 liters and about 3000 liters, between about 1500 liters and about 2500 liters. In some embodiments, the term "large volume" refers to between about 50 liters and about 2,000 liters In some embodiments, the term "large volume" refers to between about 50 liters and about 3,000 liters. In some embodiments, the term "large volume" refers to between about 50 liters and about 5,000 liters. In some embodiments, the term "large volume" refers to about 200 liters. In some embodiments, the term "large volume" refers to about 500 liters. In some embodiments, the term "large volume" refers to about 1000 liters. In some embodiments, the term "large volume" refers to about 1500 liters. In some embodiments, the term "large volume" refers to about 2000 liters. In some embodiments, the term "large volume" refers to about 2500 liters. In some embodiments, the term "large volume" refers to about 3000 liters. In some embodiments, the term "large volume" refers to about 5000 liters. In some embodiments, the term "large volume" refers to about 10000 liters. In some embodiments, the term "large volume" refers to about 15000 liters. In some embodiments, the term "large volume" refers to about 20000 liters. In some embodiments, the term "large volume" refers to between about 10 liters and 1000 liters, between about 10 liters and 100 liters, between about 20 liters and 500 liters, between about 50 liters and 500 liters, between about 100 liters and 1000 liters, or between about 100 liters and 500 liters.

rAAV Particles

The provided methods are suitable for use in the production of any isolated recombinant AAV particles. As such, the rAAV produced according to the disclosed methods can be of any serotype, modification, or derivative, known in the art, Or any combination thereof (e.g., a population of rAAV particles that comprises two or more serotypes, e.g., comprising two or more of AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other rAAV particles, or combinations of two or more thereof.

In some embodiments, rAAV particles have a capsid protein from an AAV serotype selected from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, rAAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise a capsid protein from an AAV capsid serotype selected from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16, or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise the capsid of Anc80 or Anc80L65, as described in Zinn et al., 2015, Cell Rep. 12(6): 1056-1068, which is incorporated by reference in its entirety. In certain embodiments, the rAAV particles comprise the capsid with one of the following amino acid insertions: LGETTRP or LALGETTRP, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise the capsid of AAV.7m8, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise any AAV capsid disclosed in U.S. Pat. No. 9,585,971, such as AAV-PHP.B. In some embodiments, rAAV particles comprise any AAV capsid disclosed in U.S. Pat. No. 9,840,719 and WO 2015/013313, such as AAV.Rh74 and RHM4-1, each of which is incorporated herein by reference in its entirety. In some embodiments, rAAV particles comprise any AAV capsid disclosed in WO 2014/172669, such as AAV rh.74, which is incorporated herein by reference in its entirety. In some embodiments, rAAV particles comprise the capsid of AAV2/5, as described in Georgiadis et al., 2016, Gene Therapy 23: 857-862 and Georgiadis et al., 2018, Gene Therapy 25: 450, each of which is incorporated by reference in its entirety. In some embodiments, rAAV particles comprise any AAV capsid disclosed in WO 2017/070491, such as AAV2tYF, which is incorporated herein by reference in its entirety. In some embodiments, rAAV particles comprise the capsids of AAVLKO3 or AAV3B, as described in Puzzo et al., 2017, Sci. Transl. Med. 29(9): 418, which is incorporated by reference in its entirety. In some embodiments, rAAV particles comprise any AAV capsid disclosed in U.S. Pat. Nos. 8,628,966; 8,927,514; 9,923,120 and WO 2016/049230, such as HSC1, HSC2, HSC3, HSC4, HSC5, HSC6, HSC7, HSC8, HSC9, HSC10, HSC11, HSC12, HSC13, HSC14, HSC15, or HSC16, each of which is incorporated by reference in its entirety.

In some embodiments, rAAV particles comprise an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In some embodiments, rAAV particles have a capsid protein disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689, (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10), the contents of each of which is herein incorporated by reference in its entirety. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689 (see, e.g., SEQ ID NOs: 5-38) WO2009/ 104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10).

Nucleic acid sequences of AAV based viral vectors and methods of making recombinant AAV and AAV capsids are taught, for example, in U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/ 0374803; 2015/0126588; 2017/0067908; 2013/0224836; 2016/0215024; 2017/0051257; International Patent Application Nos. PCT/US2015/034799; PCT/EP2015/053335; WO 2003/052051, WO 2005/033321, WO 03/042397, WO 2006/068888, WO 2006/110689, WO2009/104964, WO 2010/127097, and WO 2015/191508, and U.S. Appl. Publ. No. 20150023924.

The provided methods are suitable for use in the production of recombinant AAV encoding a transgene. In certain embodiments, the transgene is from Tables 1A-1C. In some embodiments, the rAAV genome comprises a vector comprising the following components: (1) AAV inverted terminal repeats that flank an expression cassette; (2) regulatory control elements, such as a) promoter/enhancers, b) a poly A signal, and c) optionally an intron; and (3) nucleic acid sequences coding for a transgene. In other embodiments for expressing an intact or substantially intact monoclonal antibody (mAb), the rAAV genome comprises a vector comprising the following components: (1) AAV inverted terminal repeats that flank an expression cassette; (2) regulatory control elements, such as a) promoter/enhancers, b) a poly A signal, and c) optionally an intron; and (3) nucleic acid sequences coding for the light chain Fab and heavy chain Fab of the antibody, or at least the heavy chain or light chain Fab, and optionally a heavy chain Fc region. In still other embodiments for expressing an intact or substantially intact mAb, the rAAV genome comprises a vector comprising the following components: (1) AAV inverted terminal repeats that flank an expression cassette; (2) regulatory control elements, such as a) promoter/enhancers, b) a poly A signal, and c) optionally an intron; and (3) nucleic acid sequences coding for the heavy chain Fab of an anti-VEGF (e.g., sevacizumab, ranibizumab, bevacizumab, and brolucizumab), anti-EpoR (e.g., LKA-651), anti-ALK1 (e.g., ascrinvacumab), anti-C5 (e.g., tesidolumab and eculizumab), anti-CD105 (e.g., carotuximab), anti-CC1Q (e.g., ANX-007), anti-TNFα (e.g., adalimumab, infliximab, and golimumab), anti-RGMa (e.g., elezanumab), anti-TTR (e.g., NI-301 and PRX-004), anti-CTGF (e.g., pamrevlumab), anti-IL6R (e.g., satralizumab and sarilumab), anti-IL4R (e.g., dupilumab), anti-IL17A (e.g., ixekizumab and secukinumab), anti-IL-5 (e.g., mepolizumab), anti-IL12/ IL23 (e.g., ustekinumab), anti-CD19 (e.g., inebilizumab), anti-ITGF7 mAb (e.g., etrolizumab), anti-SOST mAb (e.g., romosozumab), anti-pKal mAb (e.g., lanadelumab), anti-ITGA4 (e.g., natalizumab), anti-ITGA4B7 (e.g., vedolizumab), anti-BLyS (e.g., belimumab), anti-PD-1 (e.g., nivolumab and pembrolizumab), anti-RANKL (e.g., densomab), anti-PCSK9 (e.g., alirocumab and evolocumab), anti-ANGPTL3 (e.g., evinacumab*), anti-OxPL (e.g., E06), anti-fD (e.g., lampalizumab), or anti-MMP9 (e.g., andecaliximab); optionally an Fc polypeptide of the same isotype as the native form of the therapeutic antibody, such as an IgG isotype amino acid sequence IgG1, IgG2 or IgG4 or modified Fc thereof; and the light chain of an anti-VEGF (e.g., sevacizumab, ranibizumab, bevacizumab, and brolucizumab), anti-EpoR (e.g., LKA-651), anti-ALK1 (e.g., ascrinvacumab), anti-C5 (e.g., tesidolumab and eculizumab), anti-CD105 or anti-ENG (e.g., carotuximab), anti-CC1Q (e.g., ANX-007), anti-TNFα (e.g., adalimumab, infliximab, and golimumab), anti-RGMa (e.g., elezanumab), anti-TTR (e.g., NI-301 and PRX-004), anti-CTGF (e.g., pamrevlumab), anti-IL6R (e.g., satralizumab and sarilumab), anti-IL4R (e.g., dupilumab), anti-IL17A (e.g., ixekizumab and secukinumab), anti-IL-5 (e.g., mepolizumab), anti-IL12/IL23 (e.g., ustekinumab), anti-CD19 (e.g., inebilizumab), anti-ITGF7 mAb (e.g., etrolizumab), anti-SOST mAb (e.g., romosozumab), anti-pKal mAb (e.g., lanadelumab), anti-ITGA4 (e.g., natalizumab), anti-ITGA4B7 (e.g., vedolizumab), anti-BLyS (e.g., belimumab), anti-PD-1 (e.g., nivolumab and pembrolizumab), anti-RANKL (e.g., densomab), anti-PCSK9 (e.g., alirocumab and evolocumab), anti-ANGPTL3 (e.g., evinacumab), anti-OxPL (e.g., E06), anti-fD (e.g., lampalizumab), or anti-MMP9 (e.g., andecaliximab); wherein the heavy chain (Fab and optionally Fc region) and the light chain are separated by a self-cleaving furin (F)/F2A or flexible linker, ensuring expression of equal amounts of the heavy and the light chain polypeptides.

TABLE 1A

| Disease | Transgene |
| --- | --- |
| MPS I | alpha-L-iduronidase (IDUA) |
| MPS II (Hunter Syndrome) | iduronate-2-sulfatase (IDS) |
| ceroid lipofuscinosis (Batten disease) | (CLN1, CLN2, CLN10, CLN13), a soluble lysosomal protein (CLN5), a protein in the secretory pathway (CLN11), two cytoplasmic proteins that also peripherally associate with membranes (CLN4, CLN14), and many transmembrane proteins with different subcellular locations (CLN3, CLN6, CLN7, CLN8, CLN12) |

TABLE 1A-continued

| Disease | Transgene |
|---|---|
| MPS IIIa (Sanfilippo type A Syndrome) | heparan sulfate sulfatase (also called N-sulfoglucosamine sulfohydrolase (SGSH)) |
| MPS IIIB (Sanfilippo type B Syndrome) | N-acetyl-alpha-D-glucosaminidase (NAGLU) |
| MPS VI (Maroteaux-Lamy Syndrome) | arylsulfatase B |
| Gaucher disease (type 1, II and III) | Glucocerebrosidase, GBA1 |
| Parkinson's Disease | Glucocerebrosidase; GBA1 |
| Parkinson's Disease | dopamine decarboxylase |
| Pompe | acid maltase; GAA |
| Metachromatic leukodystrophy | Aryl sulfatase A |
| MPS VII (Sly syndrome) | beta-glucuronidase |
| MPS VIII | glucosamine-6-sulfate sulfatase |
| MPS IX | Hyaluronidase |
| Niemann-Pick disease | Sphingomyelinase |
| Niemann-Pick disease without sphingomyelinase deficiency | a npc1 gene encoding a cholesterol metabolizing enzyme |
| Tay-Sachs disease | Alpha subunit of beta-hexosaminidase |
| Sandhoff disease | both alpha and beta subunit of beta-hexosaminidase |
| Fabry Disease | alpha-galactosidase |
| Fucosidosis | Fucosidase (FUCA1 gene) |
| Alpha-mannosidosis | alpha-mannosidase |
| Beta-mannosidosis | Beta-mannosidase |
| Wolman disease | cholesterol ester hydrolase |
| Parkinson's disease | Neurturin |
| Parkinson's disease | glial derived growth factor (GDGF) |
| Parkinson's disease | tyrosine hydroxylase |
| Parkinson's disease | glutamic acid decarboxylase. |
| Parkinson's disease | fibroblast growth factor-2 (FGF-2) |
| Parkinson's disease | brain derived growth factor (BDGF) |
| No disease listed (Galactosialidosis (Goldberg syndrome)) | neuraminidase deficiency with betagalactosidase deficiency |
| Spinal Muscular Atrophy (SMA) | SMN |
| Friedreich's ataxia | Frataxin |
| Amyotrophic lateral sclerosis (ALS) | SOD1 |
| Glycogen Storage Disease 1a | Glucose-6-phosphatase |
| XLMTM | MTM1 |
| Crigler Najjar | UGT1A1 |
| CPVT | CASQ2 |
| Rett syndrome | MECP2 |
| Achromatopsia | CNGB3, CNGA3, GNAT2, PDE6C |
| Choroidermia | CDM |
| Danon Disease | LAMP2 |
| Cystic Fibrosis | CFTR |
| Duchenne Muscular Dystrophy | Mini- Dystrophin or Micro-Dystrophin Gene |
| Limb Girdle Muscular Dystrophy Type 2C\|Gamma-sarcoglycanopathy | human-alpha-sarcoglycan |
| Advanced Heart Failure | SERCA2a |
| Rheumatoid Arthritis | TNFR: Fc Fusion Gene |
| Leber Congenital Amaurosis | GAA |
| Limb Girdle Muscular Dystrophy Type 2C\|Gamma-sarcoglycanopathy | gamma-sarcoglycan |
| Retinitis Pigmentosa | hMERTK |
| Age-Related Macular Degeneration | sFLT01 |
| Becker Muscular Dystrophy and Sporadic Inclusion Body Myositis | huFollistatin344 |
| Parkinson's Disease | GDNF |
| Metachromatic Leukodystrophy (MLD) | cuARSA |
| Hepatitis C | anti-HCV shRNA |
| Limb Girdle Muscular Dystrophy Type 2D | hSGCA |
| Human Immunodeficiency Virus Infections; HIV Infections (HIV-1) | PG9DP |
| Acute Intermittant Porphyria | PBGD |
| Leber's Hereditary Optical Neuropathy | P1ND4v2 |
| Alpha-1 Antitrypsin Deficiency | alpha1AT |
| Pompe Disease | hGAA |
| X-linked Retinoschisis | RS1 |
| Choroideremia | hCHM |
| Giant Axonal Neuropathy | JeT-GAN |
| X-linked Retinoschisis | hRS1 |
| Squamous Cell Head and Neck Cancer; Radiation Induced Xerostomia | hAQP1 |
| Hemophilia B | Factor IX |
| Homozygous FH | hLDLR |
| Dysferlinopathies | dysferlin transgene (e.g. rAAVrh74.MHCK7.DYSF.DV) |
| Hemophilia B | AAV6 ZFP nuclease |
| MPS I | AAV6 ZFP nuclease |

TABLE 1A-continued

| Disease | Transgene |
|---|---|
| Rheumatoid Arthritis | NF-kB.IFN-β |
| Batten/CLN6 | CLN6 |
| Sanfilippo Disease Type A | hSGSH |
| Osteoarthritis | 5IL-1Ra |
| Achromatopsia | CNGA3 |
| Achromatopsia | CNGB3 |
| Ornithine Transcarbamylase (OTC) Deficiency | OTC |
| Hemophilia A | Factor VIII |
| Mucopolysaccharidosis II | ZFP nuclease |
| Hemophilia A | ZFP nuclease |
| Wet AMD | anti-VEGF |
| X-Linked Retinitis Pigmentosa | RPGR |
| Mucopolysaccharidosis Type VI | hARSB |
| Leber Hereditary Optic Neuropathy | ND4 |
| X-Linked Myotubular Myopathy | MTM1 |
| Crigler-Najjar Syndrome | UGT1A1 |
| Achromatopsia | CNGB3 |
| Retinitis Pigmentosa | hPDE6B |
| X-Linked Retinitis Pigmentosa | RPGR |
| Mucopolysaccharidosis Type 3 B | hNAGLU |
| Duchenne Muscular Dystrophy | GALGT2 |
| Arthritis, Rheumatoid; Arthritis, Psoriatic; Ankylosing Spondylitis | TNFR: Fc Fusion Gene |
| Idiopathic Parkinson's Disease | Neurturin |
| Alzheimer's Disease | NGF |
| Human Immunodeficiency Virus Infections; HIV Infections (HIV-1) | tgAAC09 |
| Familial Lipoprotein Lipase Deficiency | LPL |
| Idiopathic Parkinson's Disease | Neurturin |
| Alpha-1 Antitrypsin Deficiency | hAAT |
| Leber Congenital Amaurosis (LCA) 2 | hRPE65v2 |
| Batten Disease; Late Infantile Neuronal Lipofuscinosis | CLN2 |
| Parkinson's Disease | GAD |
| Sanfilippo Disease Type A/ Mucopolysaccharidosis Type IIIA | N-sulfoglucosamine sulfohydrolase (SGSH) gene |
| Congestive Heart Failure | SERC2a |
| Becker Muscular Dystrophy and Sporadic Inclusion Body Myositis | Follistatin (e.g. rAAV.CMV.huFollistatin344) |
| Parkinson's Disease | hAADC-2 |
| Choroideremia | REP1 |
| CEA Specific AAV-DC-CTL Treatment in Stage IV Gastric Cancer | CEA |
| Gastric Cancer | MUC1-peptide-DC-CTL |
| Leber's Hereditary Optical Neuropathy | scAAV2-P1ND4v2 |
| Aromatic Amino Acid Decarboxylase Deficiency | hAADC |
| Hemophilia B | Factor IX |
| Parkinson's Disease | AADC |
| Leber Hereditary Optic Neuropathy | Genetic: GS010\|Drug: Placebo |
| SMA—Spinal Muscular Atrophy\|Gene Therapy | SMN |
| Hemophilia A | B-Domain Deleted Factor VIII |
| MPS I | IDUA |
| MPS II | IDS |
| CLN3-Related Neuronal Ceroid- Lipofuscinosis (Batten) | CLN3 |
| Limb-Girdle Muscular Dystrophy, Type 2E | hSGCB |
| Alzheimer Disease | APOE2 |
| Retinitis Pigmentosa | hMERKTK |
| Retinitis Pigmentosa | RLBP1 |
| Wet AMD or diabetic retinopathy | Anti-VEGF antibody or Anti-VEGF trap (e.g. one or more extracellular domains of VEGFR-1 and/or VEGFR-2; e.g. aflibercept) |

TABLE 1B

| ANTIGENS | | ANTIBODIES (TRANSGENE) | INDICATIONS |
|---|---|---|---|
| Nervous System Targets | Amyloid beta (Aβ or Abeta) peptides derived from APP | Solanezumab GSK933776 | Alzheimer's Disease |
| | Sortilin | AL-001 | Frontotemporal dementia (FTD) |
| | Tau protein | ABBV-8E12 UCB-0107 NI-105 (BIIB076) | Alzheimer's, Progressive supranuclear palsy, frontotemporal demential, chronic traumatic encephalopathy, Pick's complex, primary age-related taupathy |
| | Semaphorin-4D (SEMA4D) | VX15/2503 | Huntington's disease, juvenile Huntington's disease |
| | alpha-synuclein | Prasinezumab NI-202 (BIIB054) MED-1341 | Parkinson's disease, synucleinopathies |
| | superoxide dismutase-1 (SOD-1) | NI-204 | ALS, Alzheimer's Disease |
| | CGRP Receptor | eptinezumab, fremanezumab galcanezumab | Migraines, Cluster headaches |
| Ocular Anti-Angiogenic Targets | VEGF | Sevacizumab | diabetic retinopathy (DR), myopic choroidal neovascularization (mCNV), age-related macular degeneration (AMD), macular edema |
| | VEGF | ranibizumab (LUCENTIS ®) bevacizumab (AVASTIN ®) brolucizumab | Wet AMD |
| | erythropoietin receptor | LKA-651 | retinal vein occlusion (RVO), wet AMD, macular edema |
| | Amyloid beta (Aβ or Abeta) peptides derived from APP | Solanezumab GSK933776 | Dry AMD |
| | activin receptor like kinase 1 (ALK1) | ascrinvacumab | neovascular age-related macular degeneration |
| | complement component 5 (C5) | tesidolumab | dry AMD, uveitis |
| | endoglin (END or CD105) | carotuximab | wet AMD and other retinal disorders caused by increased vascularization |
| | complement component 1Q (C1Q) | ANX-007 | glaucoma |
| | TNF-alpha | adalimumab (HUMIRA ®) infliximab (REMICADE ®) golimumab | uveitis |
| | Repulsive guidance molecule-A | elezanumab | multiple sclerosis |
| | Transthyretin (TTR) | NI-301 PRX-004 | amyloidosis |
| | Connective tissue growth factor (CTGF) | pamrevlumab | fibrotic diseases, e.g. diabetic nephropathy, liver fibrosis, idiopathic pulmonary fibrosis |
| Neuromyelitis optica (NMO)/ Uveitis targets | interleukin receptor 6 (IT6R) | Satralizumab sarilumab | NMO, DR, DME, uveitis |
| | CD19 | inebilizumab | NMO |
| | Integrin beta 7 | etrolizumab | ulcerative colitis, Crohn's disease |

TABLE 1B-continued

| ANTIGENS | ANTIBODIES (TRANSGENE) | INDICATIONS |
|---|---|---|
| Sclerostin | romosozumab (EVENITY ®) | Osteoporosis, abnormal bone loss or weakness |

TABLE 1C

| | ANTIGENS | ANTIBODIES (TRANSGENE) | INDICATIONS |
|---|---|---|---|
| Nervous System Targets | Amyloid beta (Aβ or Abeta) peptides | Aducanumab crenezumab gantenerumab | Alzheimer's Disease |
| | Tau protein | anti-TAU | Alzheimer's, Progressive supranuclear palsy, frontotemporal demential, chronic traumatic encephalopathy, Pick's complex, primary age-related taupathy |
| | CGRP Receptor | erenumab (AIMOVIG ™) | Migraine |
| Interleukins or interleukin receptors | IL-17A | ixekizumab (TALTZ ®) secukinumab (COSENTYX ®) | Plaque psoriasis, psoriatic arthritis, ankylosing sponylitis |
| | IL-5 | mepolizumab (NUCALA ®) | Asthma |
| | IL-12/IL-23 | ustekinumab (STELARA ®) | Psoriasis & Crohn's disease |
| | IL-4R | dupilumab | Atopic dermatitis |
| | Integrin | vedolizumab (ENTYVIO ®) | Ulcerative colitis & Crohn's disease |
| | | Natalizumab (anti-integrin alpha 4) | Multiple sclerosis & Crohn's disease |
| Cardiovascular Targets | PCSK9 | alirocumab (PRALUENT ®) evolucomab (REPATHA ®) | HeFH & HoFH |
| | ANGPTL3 | evinacumab | HoFH & severe forms of dyslipidema |
| | Proinflammatory proatherogenic phospholipids | E06-scFv | Cardiovascular diseases such as atherosclerosis |
| | RANKL | denosumab (XGEVA ® and PROLIA ®) | Osteoporosis, increasing bone mass in breast and prostate cancer patients, & preventing skeletal-related events due to bone metastasis |
| | PD-1, or PD-L1 or PD-L2 | nivolumab (OPDIVO ®) pembrolizumab (KEYTRUDA ®) | Metastatic melanoma, lymphoma, non-small cell lung carcinoma |
| | BLyS (B-lymphocyte stimulator, also known as B-cell activating factor (BAFF)) | belimumab (BENLYSTA ®) | Systemic lupus erythromatosis |
| Ocular Targets | Factor D | lampalizumab | Dry AMD |
| | MMP9 | andecaliximab | Dry AMD |
| | TNF-alpha | adalimumab (HUMIRA ®) and infliximab (REMICADE ®) | Rheumatoid arthritis, psoriatic arthritis, askylosing spondylitis, Crohn's disease, plaque psoriasis, ulcerative colitis |
| Plasma Protein targets | C5, C5a | eculizumab (SOLIRIS ®) | Paroxysmal nocturnal hemoglobinuria, atypical hemolytic uremic syndrome, complement-mediated thrombotic microangiopathy |
| | Plasma kallikrein | lanadelumab | Hereditary angioedema (HAE) |

In some embodiments, provided herein are rAAV viral vectors encoding an anti-VEGF Fab. In specific embodiments, provided herein are rAAV8-based viral vectors encoding an anti-VEGF Fab. In more specific embodiments, provided herein are rAAV8-based viral vectors encoding ranibizumab. In some embodiments, provided herein are rAAV viral vectors encoding iduronidase (IDUA). In specific embodiments, provided herein are rAAV9-hased viral vectors encoding IDUA. In some embodiments, provided herein are rAAV viral vectors encoding iduronate 2-sulfatase (IDS). In specific embodiments, provided herein are rAAV9-based viral vectors encoding IDS. In some embodiments, provided herein are rAAV viral vectors encoding a low-density lipoprotein receptor (LDLR). In specific embodiments, provided herein are rAAV8-based viral vectors encoding LDLR. In some embodiments, provided herein are rAAV viral vectors encoding tripeptidyl peptidase 1 (TPP1) protein. In specific embodiments, provided herein are rAAV9-based viral vectors encoding TPP1. In some embodiments, provided herein are rAAV viral vectors encoding non-membrane associated splice variant of VEGF receptor 1 (sFlt-1). In some embodiments, provided herein are rAAV viral vectors encoding gamma-sarcoglycan, Rab Escort Protein 1 (REP1/CHM), retinoid isomerohydrolase (RPE65), cyclic nucleotide gated channel alpha 3 (CNGA3), cyclic nucleotide gated channel beta 3 (CNGB3), aromatic L-amino acid decarboxylase (AADC), lysosome-associated membrane protein 2 isoform B (LAMP2B), Factor VIII, Factor IX, retinitis pigmentosa GTPase regulator (RPGR), retinoschisin (RS1), sarcoplasmic reticulum calcium ATPase (SERCA2a), aflibercept, battenin (CLN3), transmembrane ER protein (CLN6), glutamic acid decarboxylase (GAD), Glial cell line-derived neurotrophic factor (GDNF), aquaporin 1 (AQP1), dystrophin, myotubularin 1 (MTM1), follistatin (FST), glucose-6-phosphatase (G6Pase), apolipoprotein A2 (APOA2), uridine diphosphate glucuronosyl transferase 1A1 (UGT1A1), arylsulfatase B (ARSB), N-acetyl-alpha-glucosaminidase (NAGLU), alpha-glucosidase (GAA), alpha-galactosidase (GLA), beta-galactosidase (GLB1), lipoprotein lipase (LPL), alpha 1-antitrypsin (AAT), phosphodiesterase 6B (PDE6B), ornithine carbamoyltransferase 90TC), survival motor neuron (SMN1), survival motor neuron (SMN2), neurturin (NRTN), Neurotrophin-3 (NT-3/NTF3), porphobilinogen deaminase (PBGD), nerve growth factor (NGF), mitochondrially encoded NADH:ubiquinone oxidoreductase core subunit 4 (MT-ND4), protective protein cathepsin A (PPCA), dysferlin, MER proto-oncogene, tyrosine kinase (MERTK), cystic fibrosis transmembrane conductance regulator (CFTR), or tumor necrosis factor receptor (TNFR)-immunoglobulin (IgG1) Fc fusion.

In additional embodiments, rAAV particles comprise a pseudotyped AAV capsid. In some embodiments, the pseudotyped AAV capsids are rAAV2/8 or rAAV2/9 pseudotyped AAV capsids. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In some embodiments, the capsid protein is a chimeric of 2 or more AAV capsid proteins from AAV serotypes selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In certain embodiments, a single-stranded AAV (ssAAV) can be used. In certain embodiments, a self-complementary vector, e.g., scAAV, can be used (see, e.g., Wu, 2007, Human Gene Therapy, 18(2):171-82, McCarty et al, 2001, Gene Therapy, Vol. 8, Number 16, Pages 1248-1254; and U.S. Pat. Nos. 6,596,535; 7,125,717; and 7,456,683, each of which is incorporated herein by reference in its entirety).

In some embodiments, rAAV particles comprise a capsid protein from an AAV capsid serotype selected from AAV8 or AAV9. In some embodiments, the rAAV particles comprise a capsid protein from an AAV capsid serotype selected from the group consisting of AAV.rh8, AAV.rh10, AAV.rh20, AAV.rh39, AAV.Rh74, AAV.RHM4-1, AAV.hu37, AAV.PHB, and AAV.7m8. In some embodiments, the rAAV particles comprise a capsid protein with high sequence homology to AAV8 or AAV9 such as, AAV.rh10, AAV.rh20, AAV.rh39, AAV.Rh74, AAV.RHM4-1, and AAV.hu37. In some embodiments, the rAAV particles have an AAV capsid serotype of AAV1 or a derivative, modification, or pseudotype thereof. In some embodiments, the rAAV particles have an AAV capsid serotype of AAV4 or a derivative, modification, or pseudotype thereof. In some embodiments, the rAAV particles have an AAV capsid serotype of AAV5 or a derivative, modification, or pseudotype thereof. In some embodiments, the rAAV particles have an AAV capsid serotype of AAV8 or a derivative, modification, or pseudotype thereof. In some embodiments, the rAAV particles have an AAV capsid serotype of AAV9 or a derivative, modification, or pseudotype thereof.

In some embodiments, rAAV particles comprise a capsid protein that is a derivative, modification, or pseudotype of AAV8 or AAV9 capsid protein. In some embodiments, rAAV particles comprise a capsid protein that has an AAV8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV8 capsid protein.

In some embodiments, rAAV particles comprise a capsid protein that is a derivative, modification, or pseudotype of AAV9 capsid protein. In some embodiments, rAAV particles comprise a capsid protein that has an AAV8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV9 capsid protein.

In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of AAV.rh8, AAV.rh10, AAV.rh20, AAV.rh39, AAV.Rh74, AAV.RHM4-1, AAV.hu37, AAV.PHB, or AAV.7m8 capsid protein. In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of an AAV capsid protein with high sequence homology to AAV8 or AAV9 such as, AAV.rh10, AAV.rh20, AAV.rh39, AAV.Rh74, AAV.RHM4-1, and AAV.hu37.

In additional embodiments, rAAV particles comprise a mosaic capsid. Mosaic AAV particles are composed of a mixture of viral capsid proteins from different serotypes of AAV. In some embodiments, rAAV particles comprise a mosaic capsid containing capsid proteins of a serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, rAAV particles comprise a mosaic capsid containing capsid proteins of a serotype selected from AAV1, AAV2, AAV5, AAV6, AAV7, AAV8, AAV9, AAV10, AAVrh.8, and AAVrh.10.

In additional embodiments, rAAV particles comprise a pseudotyped rAAV particle. In some embodiments, the pseudotyped rAAV particle comprises (a) a nucleic acid vector comprising AAV ITRs and (b) a capsid comprised of capsid proteins derived from AAVx (e.g., AAV1, AAV3, AAV4, AAV5, AAV6, AAV7, AAV8, AAV9, AAV10 AAV11, AAV12, AAV13, AAV14, AAV15 and AAV16). In additional embodiments, rAAV particles comprise a pseudo- typed rAAV particle comprised of a capsid protein of an AAV serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In additional embodiments, rAAV particles comprise a pseudotyped rAAV particle containing AAV8 capsid protein. In additional embodiments, rAAV particles comprise a pseudotyped rAAV particle is comprised of AAV9 capsid protein. In some embodiments, the pseudotyped rAAV8 or rAAV9 particles are rAAV2/8 or rAAV2/9 pseudotyped particles. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158- 167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In further embodiments, the capsid protein is a chimeric of 2 or more AAV capsid proteins from AAV serotypes selected from AAV1, AAV2, rAAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, rAAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In further embodiments, the capsid protein is a chimeric of 2 or more AAV capsid proteins from AAV serotypes selected from AAV1, AAV2, AAV5, AAV6, AAV7, AAV8, AAV9, AAV10, AAVrh.8, and AAVrh.10.

In some embodiments, the rAAV particles comprise an AAV capsid protein chimeric of AAV8 capsid protein and one or more AAV capsid proteins from an AAV serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV8 capsid protein and one or more AAV capsid proteins from an AAV serotype selected from AAV1, AAV2, AAV5, AAV6, AAV7, AAV9, AAV10, AAVrh.8, and AAVrh.10.

In some embodiments, the rAAV particles comprise an AAV capsid protein chimeric of AAV9 capsid protein the capsid protein of one or more AAV capsid serotypes selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, the rAAV particles comprise an AAV capsid protein chimeric of AAV9 capsid protein the capsid protein of one or more AAV capsid serotypes selected from AAV1, AAV2, AAV3, AAV4, AAV5, AA6, AAV7, AAV8, AAV9, AAVrh.8, and AAVrh.10

Methods for Isolating rAAV Particles

Methods of producing rAAV particles disclosed herein (e.g., the method of any one of [1]-[129]) can be used in combination with upstream processing to isolate rAAV particles.

The rAAV particles produced according to a method disclosed herein (e.g., the method of any one of [1]-[129]) can be isolated using methods known in the art. In some embodiments, methods of isolating rAAV particles produced according to a method disclosed herein comprises down- stream processing such as, for example, harvest of a cell culture, clarification of the harvested cell culture (e.g., by centrifugation or depth filtration), tangential flow filtration, affinity chromatography, anion exchange chromatography, cation exchange chromatography, size exclusion chromatog- raphy, hydrophobic interaction chromatography, hydroxy- lapatite chromatography, sterile filtration, or any combina- tion(s) thereof. In some embodiments, downstream processing includes at least 2, at least 3, at least 4, at least 5 or at least 6 of: harvest of a cell culture, clarification of the harvested cell culture (e.g., by centrifugation or depth fil- tration), tangential flow filtration, affinity chromatography, anion exchange chromatography, cation exchange chroma- tography, size exclusion chromatography, hydrophobic interaction chromatography, hydroxylapatite chromatogra- phy, and sterile filtration. In some embodiments, down- stream processing comprises harvest of a cell culture, clarification of the harvested cell culture (e.g., by depth filtration), sterile filtration, tangential flow filtration, affinity chromatography, and anion exchange chromatography. In some embodiments, downstream processing comprises clarification of a harvested cell culture, sterile filtration, tangential flow filtration, affinity chromatography, and anion exchange chromatography. In some embodiments, downstream processing comprises clarification of a harvested cell culture by depth filtration, sterile filtration, tangential flow filtration, affinity chromatography, and anion exchange chromatography. In some embodiments, clarification of the harvested cell culture comprises sterile filtration. In some embodiments, downstream processing does not include centrifugation. In some embodiments, the rAAV particles comprise a capsid protein of the AAV8 serotype. In some embodiments, the rAAV particles comprise a capsid protein of the AAV9 serotype.

In some embodiments, a method of isolating rAAV particles produced according to a method disclosed herein comprises harvest of a cell culture, clarification of the harvested cell culture (e.g., by depth filtration), a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method of isolating rAAV particles disclosed herein comprises harvest of a cell culture, clarification of the harvested cell culture (e.g., by depth filtration), a first sterile filtration, affinity chromatography, anion exchange chromatography (e.g., monolith anion exchange chromatography or AEX chromatography using a quaternary amine ligand), a tangential flow filtration, and a second sterile filtration. In some embodiments, a method of isolating rAAV particles produced according to a method disclosed herein comprises clarification of a harvested cell culture, a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method of isolating rAAV particles disclosed herein comprises clarification of a harvested cell culture, a first sterile filtration, affinity chromatography, anion exchange chromatography (e.g., monolith anion exchange chromatography or AEX chromatography using a quaternary amine ligand), tangential flow filtration, and a second sterile filtration. In some embodiments, a method of isolating rAAV particles produced according to a method disclosed herein comprises clarification of a harvested cell culture by depth filtration, a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method of isolating rAAV particles disclosed herein comprises clarification of a harvested cell culture by depth filtration, a first sterile filtration, affinity chromatography, anion exchange chromatography (e.g., monolith anion exchange chromatography or AEX chromatography using a quaternary amine ligand), tangential flow filtration, and a second sterile filtration. In some embodiments, the method does not include centrifugation. In some embodiments, clarification of the harvested cell culture comprises sterile filtration. In some embodiments, the rAAV particles comprise a capsid protein of the AAV8 serotype. In some embodiments, the rAAV particles comprise a capsid protein of the AAV9 serotype.

Numerous methods are known in the art for production of rAAV particles, including transfection, stable cell line production, and infectious hybrid virus production systems which include Adenovirus-AAV hybrids, herpesvirus-AAV hybrids and baculovirus-AAV hybrids. rAAV production cultures for the production of rAAV virus particles all require; (1) suitable host cells, including, for example, human-derived cell lines such as HeLa, A549, or HEK293 cells and their derivatives (HEK293T cells, HEK293F cells), mammalian cell lines such as Vero, or insect-derived cell lines such as SF-9 in the case of baculovirus production systems; (2) suitable helper virus function, provided by wild type or mutant adenovirus (such as temperature sensitive adenovirus), herpes virus, baculovirus, or a plasmid construct providing helper functions; (3) AAV rep and cap genes and gene products; (4) a transgene (such as a therapeutic transgene) flanked by AAV ITR sequences; and (5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), and Sf-900 II SFM media as described in U.S. Pat. No. 6,723,551, which is incorporated herein by reference in its entirety.

rAAV production cultures can routinely be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa cells, HEK293 cells, HEK293 derived cells (e.g., HEK293T cells, HEK293F cells), Vero cells, CHO cells, CHO-K1 cells, CHO derived cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells or SF-9 cells which can be cultured in a variety of ways including, for example, spinner flasks, stirred tank bioreactors, and disposable systems such as the Wave bag system. In some embodiments, the cells are HEK293 cells. In some embodiments, the cells are HEK293 cells adapted for growth in suspension culture. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety.

In some embodiments, the rAAV production culture comprises a high density cell culture. In some embodiments, the culture has a total cell density of between about $1\times10E+06$ cells/ml and about $30\times10E+06$ cells/ml. In some embodiments, more than about 50% of the cells are viable cells. In some embodiments, the cells are HeLa cells, HEK293 cells, HEK293 derived cells (e.g., HEK293T cells, HEK293F cells), Vero cells, or SF-9 cells. In further embodiments, the cells are HEK293 cells. In further embodiments, the cells are HEK293 cells adapted for growth in suspension culture.

In additional embodiments of the provided method the rAAV production culture comprises a suspension culture comprising rAAV particles. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety. In some embodiments, the suspension culture comprises a culture of mammalian cells or insect cells. In some embodiments, the suspension culture comprises a culture of HeLa cells, HEK293 cells, HEK293 derived cells (e.g., HEK293T cells, HEK293F cells), Vero cells, CHO cells, CHO-K1 cells, CHO derived cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells or SF-9 cells. In some embodiments, the suspension culture comprises a culture of HEK293 cells.

Recombinant AAV particles can be harvested from rAAV production cultures by harvest of the production culture comprising host cells or by harvest of the spent media from the production culture, provided the cells are cultured under conditions known in the art to cause release of rAAV particles into the media from intact host cells. Recombinant AAV particles can also be harvested from rAAV production cultures by lysis of the host cells of the production culture. Suitable methods of lysing cells are also known in the art and include for example multiple freeze/thaw cycles, sonication, microfluidization, and treatment with chemicals, such as detergents and/or proteases.

At harvest, rAAV production cultures can contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins. rAAV production cultures can further contain product-related impurities, for example, inactive vector forms, empty viral capsids, aggregated viral particles or capsids, mis-folded viral capsids, degraded viral particle.

In some embodiments, the rAAV production culture harvest is clarified to remove host cell debris. In some embodiments, the production culture harvest is clarified by filtration through a series of depth filters. Clarification can also be achieved by a variety of other standard techniques known in the art, such as, centrifugation or filtration through any cellulose acetate filter of 0.2 mm or greater pore size known in the art. In some embodiments, clarification of the harvested cell culture comprises sterile filtration. In some embodiments, the production culture harvest is clarified by centrifugation. In some embodiments, clarification of the production culture harvest does not included centrifugation.

In some embodiments, harvested cell culture is clarified using filtration. In some embodiments, clarification of the harvested cell culture comprises depth filtration. In some embodiments, clarification of the harvested cell culture further comprises depth filtration and sterile filtration. In some embodiments, harvested cell culture is clarified using a filter train comprising one or more different filtration media. In some embodiments, the filter train comprises a depth filtration media. In some embodiments, the filter train comprises one or more depth filtration media. In some embodiments, the filter train comprises two depth filtration media. In some embodiments, the filter train comprises a sterile filtration media. In some embodiments, the filter train comprises 2 depth filtration media and a sterile filtration media. In some embodiments, the depth filter media is a porous depth filter. In some embodiments, the filter train comprises Clarisolve® 20MS, Millistak+® COHC, and a sterilizing grade filter media. In some embodiments, the filter train comprises Clarisolve® 20MS, Millistak+® COHC, and Sartopore® 2 XLG 0.2 µm. In some embodiments, the harvested cell culture is pretreated before contacting it with the depth filter. In some embodiments, the pretreating comprises adding a salt to the harvested cell culture. In some embodiments, the pretreating comprises adding a chemical flocculent to the harvested cell culture. In some embodiments, the harvested cell culture is not pretreated before contacting it with the depth filter.

In some embodiments, the production culture harvest is clarified by filtration are disclosed in PCT International Patent Application No. PCT/US2019/029539, filed on Apr. 27, 2019, titled "SCALABLE CLARIFICATION PROCESS FOR RECOMBINANT AAV PRODUCTION," which is incorporated herein by reference in its entirety.

In some embodiments, the rAAV production culture harvest is treated with a nuclease (e.g., Benzonase®) or endonuclease (e.g., endonuclease from *Serratia marcescens*) to digest high molecular weight DNA present in the production culture. The nuclease or endonuclease digestion can routinely be performed under standard conditions known in the art. For example, nuclease digestion is performed at a final concentration of 1-2.5 units/ml of Benzonase® at a temperature ranging from ambient to 37° C. for a period of 30 minutes to several hours.

Sterile filtration encompasses filtration using a sterilizing grade filter media. In some embodiments, the sterilizing grade filter media is a 0.2 or 0.22 µm pore filter. In some embodiments, the sterilizing grade filter media comprises polyethersulfone (PES). In some embodiments, the sterilizing grade filter media comprises polyvinylidene fluoride (PVDF). In some embodiments, the sterilizing grade filter media has a hydrophilic heterogeneous double layer design. In some embodiments, the sterilizing grade filter media has a hydrophilic heterogeneous double layer design of a 0.8 µm pre-filter and 0.2 µm final filter membrane. In some embodiments, the sterilizing grade filter media has a hydrophilic heterogeneous double layer design of a 1.2 µm pre-filter and 0.2 µm final filter membrane. In some embodiments, sterilizing grade filter media is a 0.2 or 0.22 µm pore filter. In further embodiments, the sterilizing grade filter media is a 0.2 µm pore filter. In some embodiments, the sterilizing grade filter media is a Sartopore® 2 XLG 0.2 µm, Durapore™ PVDF Membranes 0.45 µm, or Sartoguard® PES 1.2 m+0.2 m nominal pore size combination. In some embodiments, the sterilizing grade filter media is a Sartopore® 2 XLG 0.2 µm.

In some embodiments, the clarified feed is concentrated via tangential flow filtration ("TFF") before being applied to a chromatographic medium, for example, affinity chromatography medium. Large scale concentration of viruses using TFF ultrafiltration has been described by Paul et al., Human Gene Therapy 4:609-615 (1993). TFF concentration of the clarified feed enables a technically manageable volume of clarified feed to be subjected to chromatography and allows for more reasonable sizing of columns without the need for lengthy recirculation times. In some embodiments, the clarified feed is concentrated between at least two-fold and at least ten-fold. In some embodiments, the clarified feed is concentrated between at least ten-fold and at least twenty-fold. In some embodiments, the clarified feed is concentrated between at least twenty-fold and at least fifty-fold. In some embodiments, the clarified feed is concentrated about twenty-fold. One of ordinary skill in the art will also recognize that TFF can also be used to remove small molecule impurities (e.g., cell culture contaminants comprising media components, serum albumin, or other serum proteins) form the clarified feed via diafiltration. In some embodiments, the clarified feed is subjected to diafiltration to remove small molecule impurities. In some embodiments, the diafiltration comprises the use of between about 3 and about 10 diafiltration volume of buffer. In some embodiments, the diafiltration comprises the use of about 5 diafiltration volume of buffer. One of ordinary skill in the art will also recognize that TFF can also be used at any step in the purification process where it is desirable to exchange buffers before performing the next step in the purification process. In some embodiments, the methods for isolating rAAV from the clarified feed disclosed herein comprise the use of TFF to exchange buffers.

Affinity chromatography can be used to isolate rAAV particles from a composition. In some embodiments, affinity chromatography is used to isolate rAAV particles from the clarified feed. In some embodiments, affinity chromatography is used to isolate rAAV particles from the clarified feed that has been subjected to tangential flow filtration. Suitable affinity chromatography media are known in the art and include without limitation, AVB Sepharose™, POROS™ CaptureSelect™ AAVX affinity resin, POROS™ Capture-Select™ AAV9 affinity resin, and POROS™ CaptureSe-lect™ AAV8 affinity resin. In some embodiments, the affinity chromatography media is POROS™ CaptureSelect™ AAV9 affinity resin. In some embodiments, the affinity chromatography media is POROS™ CaptureSelect™ AAV8 affinity resin. In some embodiments, the affinity chromatography media is POROS™ CaptureSelect™ AAVX affinity resin.

Anion exchange chromatography can be used to isolate rAAV particles from a composition. In some embodiments, anion exchange chromatography is used after affinity chromatography as a final concentration and polish step. Suitable anion exchange chromatography media are known in the art and include without limitation, UNOsphere™ Q (strong anion exchange matrix with quaternary ammonium; Biorad, Hercules, Calif.), and N-charged amino or imino resins such as e.g., POROS 50 PI, or any DEAE, TMAE, tertiary or quaternary amine, or PEI-based resins known in the art (U.S. Pat. No. 6,989,264; Brument et al., Mol. Therapy 6(5):678-686 (2002); Gao et al., Hum. Gene Therapy 11:2079-2091 (2000)). In some embodiments, the anion exchange chromatography media comprises a quaternary amine. In some embodiments, the anion exchange media is a monolith anion exchange chromatography resin. In some embodiments, the monolith anion exchange chromatography media comprises glycidylmethacrylate-ethylenedimethacrylate or styrene-divinylbenzene polymers. In some embodiments, the monolith anion exchange chromatography media is selected from the group consisting of CIMmultus™ QA-1 Advanced Composite Column (Quaternary amine), CIMmultus™ DEAE-1 Advanced Composite Column (Diethylamino), CIM® QA Disk (Quaternary amine), CIM® DEAE, and CIM® EDA Disk (Ethylene diamino). In some embodiments, the monolith anion exchange chromatography media is CIMmultus™ QA-1 Advanced Composite Column (Quaternary amine). In some embodiments, the monolith anion exchange chromatography media is CIM® QA Disk (Quaternary amine). In some embodiments, the anion exchange chromatography media is CIM® QA (BIA Separations, Slovenia). In some embodiments, the anion exchange chromatography media is BIA CIM® QA-80 (Column volume is 80 mL). One of ordinary skill in the art can appreciate that wash buffers of suitable ionic strength can be identified such that the rAAV remains bound to the resin while impurities, including without limitation impurities which may be introduced by upstream purification steps are stripped away.

In some embodiments, anion exchange chromatography is performed according to a method disclosed in U.S. Provisional Application No. 62/684,835, filed on Jun. 14, 2018, titled "Anion Exchange Chromatography for Recombinant AAV production," which is incorporated herein by reference in its entirety.

In additional embodiments the disclosure provides compositions comprising isolated rAAV particles produced according to a method disclosed herein. In some embodiment, the composition is a pharmaceutical composition comprising a pharmaceutically acceptable carrier.

As used herein the term "pharmaceutically acceptable means a biologically acceptable formulation, gaseous, liquid or solid, or mixture thereof, which is suitable for one or more routes of administration, in vivo delivery or contact. A "pharmaceutically acceptable" composition is a material that is not biologically or otherwise undesirable, e.g., the material may be administered to a subject without causing substantial undesirable biological effects. Thus, such a pharmaceutical composition may be used, for example in administering rAAV isolated according to the disclosed methods to a subject. Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions. Pharmaceutical compositions can be formulated to be compatible with a particular route of administration or delivery, as set forth herein or known to one of skill in the art. Thus, pharmaceutical compositions include carriers, diluents, or excipients suitable for administration by various routes. Pharmaceutical compositions and delivery systems appropriate for rAAV particles and methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

In some embodiments, the composition is a pharmaceutical unit dose. A "unit dose" refers to a physically discrete unit suited as a unitary dosage for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dose forms may be within, for example, ampules and vials, which may include a liquid composition, or a composition in a freeze-dried or lyophilized state; a sterile liquid carrier, for example, can be added prior to administration or delivery in vivo. Individual unit dose forms can be included in multi-dose kits or containers. Recombinant vector (e.g., AAV) sequences, plasmids, vector genomes, and recombinant virus particles, and pharmaceutical compositions thereof can be packaged in single or multiple unit dose form for ease of administration and uniformity of dosage. In some embodiments, the composition comprises rAAV particles comprising an AAV capsid protein from an AAV capsid serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the AAV capsid serotype is AAV8. In some embodiments, the AAV capsid serotype is AAV9.

EXAMPLES

Example 1. Effect of Sodium Chloride, Sodium Butyrate, and/or Sodium Valproate on rAAV Yield The effect of sodium chloride, sodium butyrate, and/or sodium valproate on rAAV yield in a HEK293 suspension cell based process was tested. HEK293 cells were seeded at 1×10e6 viable cell/ml density in advanced microscale bioreactors. The medium comprised 100 mM NaCl. At 48 hrs ECD (Elapsed Culture Duration), the cells were transfected with a mixture of polyethylenimine and 3 plasmids encoding adeno-virus helper functions, transgene and AAV 2/8 Rep/Cap. 24 hours after transfection, NaCl, Na butyrate, and/or Na valproate was added to the cultures. Conditions tested were 0, 25 mM and 90 mM NaCl, 0, 2 mM and 4 mM Na butyrate, and 0, 1.5 mM and 3 mM Na valproate. A full factorial combination of the conditions were tested using 36 reaction conditions. The supernatant of the cultures was harvested at 168 hours ECD, i.e., 5 days post-transfection. A significant improvement in virus yield was obtained by adding 60 mM of sodium chloride, and either 4 mM sodium butyrate or 3 mM sodium valproate on 1 day post transfection.

Example 2. Effect of Sodium Chloride and/or Sodium Valproate on rAAV Yield

The effect of sodium chloride, sodium valproate and combinations thereof added a different times on rAAV yield in a HEK293 suspension cell based process was tested. HEK293 suspension cells were seeded at 1×10e6 viable cell/ml density in advanced microscale bioreactors. The medium comprised 100 mM NaCl. At 48 hrs ECD (Elapsed Culture Duration), the cells were transfected with a mixture of polyethylenimine and 3 plasmids encoding adeno-virus helper functions, transgene and AAV 2/8 Rep/Cap. NaCl and/or Na valproate was added to the cultures at 4 hrs, 24 hrs or 48 hrs post-transfection. NaCl and Na valproate concentrations tested were 0, 30 mM and 60 mM NaCl, and 0, 1 mM and 2 mM Na valproate. The supernatant of the cultures was harvested at 168 hours ECD, i.e., 5 days post-transfection. rAAV yields obtained are shown in FIG. 1. 24 different conditions were tested and analyzed using a Design of Experiment strategy. The model generated from the 24-condition DOE testing predicted that the addition of 2 mM Na valproate at 4 hours post transfection followed by 30 mM NaCl at 24 hours post transfection significantly boosts virus yield.

Example 3. Large Scale Production of rAAV Using NaCl Enhancer

The effect of NaCl on rAAV yield was tested in 50 liter cultures of HEK293 cells expressing AAV8 particles encapsidating a transgene. HEK suspension cultures were grown using standard processes. Cells were diluted to ~4×10e6 viable cells. The medium used included 100 mM NaCl. Cells were transfected 24 hours post dilution with a mixture of polyethylenimine and 3 plasmids encoding adeno-virus helper functions, transgene and AAV Cap/Rev. 24 hours post transfection, sufficient NaCl was added to increase the final NaCl concentration by 60 mM. (i.e., the final NaCl concentration was ~160 mM). Supernatant was harvested on day 4 post transfection. The processes yielded 1×10e+11 genome copy (GC)/ml and 9×10e+10. This is ~2-fold higher than the yield of the same process without the increase in NaCl concentration following transfection.

Example 4. Large Scale Production of AAV Using NaCl and Sodium Propionate

The effect of NaCl on rAAV yield was tested in 50 liter cultures of HEK293 cells expressing AAV8 particles encapsidating a transgene. HEK suspension cultures were grown using standard processes. Cells were diluted to ~4×10e6 viable cells. The medium used included 100 mM NaCl. Cells were transfected 24 hours post dilution with a mixture of polyethylenimine and 3 plasmids encoding adeno-virus helper functions, transgene and AAV 2/8 Rep/Cap. 24 hours post transfection, sufficient NaCl was added to increase the final NaCl concentration by 30 mM. (i.e., the final NaCl concentration was ~130 mM) and sufficient sodium propionate (NaPr) was added to increase the final NaPr concentration to 2 mM (no NaPr is in the medium at start). Supernatant was harvested on day 4 post transfection. The processes yielded 1×10e+11 genome copy (GC)/ml. This was ~1.7-fold higher than the yield of the same process without the increases in NaCl and NaPr concentration following transfection. FIG. 2. Also, titer was significantly increased without sacrificing quality. Product quality e.g. % full capsids, % fragmented rAAV, and residual DNA such as residual 18S (the gene for 18S RNA used to estimate residual mammalian genomic DNA), residual E1a, and residual plasmid, were not negatively affected by the scale up production process with enhancers compared to an analogous process without enhancers.

Example 5. Effect of Sodium Chloride and/or Sodium Propionate on rAAV Yield

Figure 3:
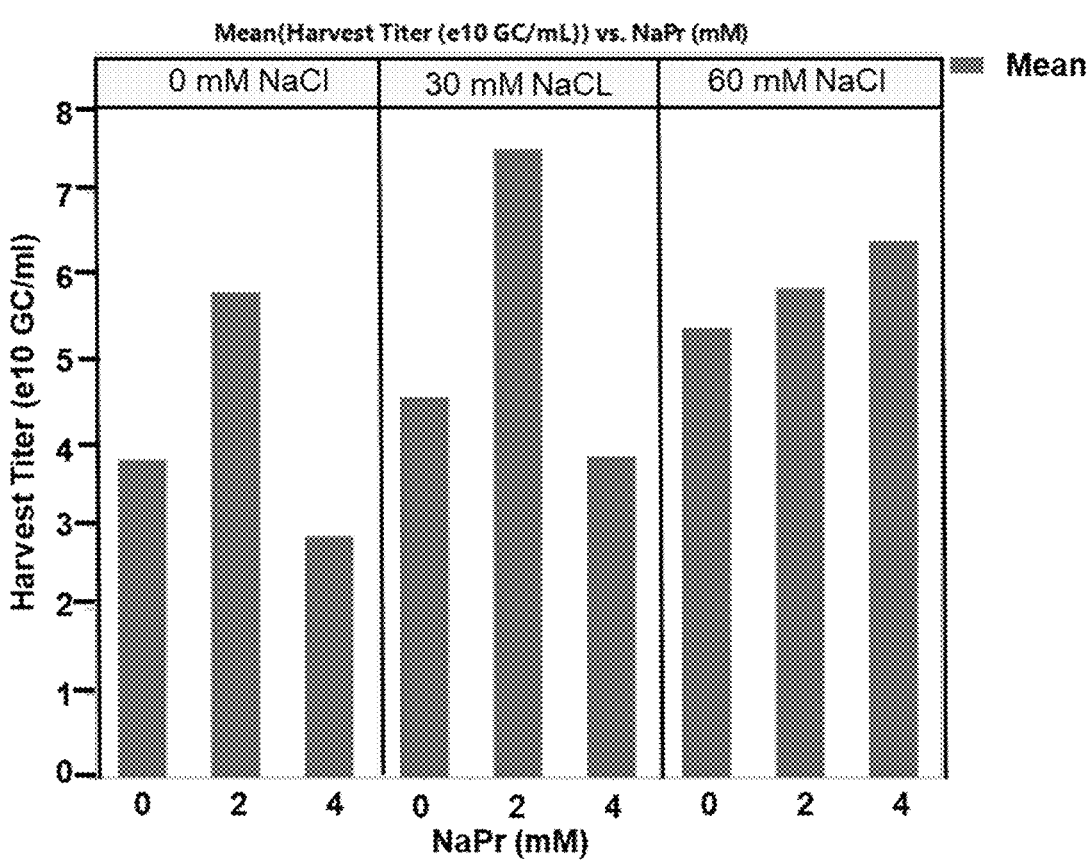
FIG. 3. rAAV9 yields obtained following the addition of sodium chloride, and/or sodium propionate.

The effect of sodium chloride and sodium propionate (NaPr) (ThermoFisher Scientific) on rAAV yield in a suspension culture of HEK293 cells expressing rAAV9 particles encapsidating a transgene. HEK293 cells were seeded at 1×10e6 viable cell/ml density in advanced microscale bioreactors. The medium comprised 100 mM NaCl. At 48 hrs ECD (Elapsed Culture Duration), the cells were transfected with a mixture of polyethylenimine and 3 plasmids encoding adeno-virus helper functions, transgene and AAV 2/9 Rep/Cap. 4, 20, or 36 hours after transfection, NaCl, NaPr, anti-clump, EFC+, and/or Na valproate was added to the cultures. Conditions tested were 0, 30 mM and 60 mM NaCl, 0, 2 mM and 4 mM NaPr. Multiple conditions were tested using a Design of Experiment approach. The supernatant of the cultures was harvested at 168 hours ECD, i.e., 5 days post-transfection. rAAV yields were obtained. A significant and synergistic improvement in virus yield was obtained by adding both 30 mM of sodium chloride and 2 mM sodium propionate 20 hours post transfection. Resulting titer improvement by adding NaCl and/or NaPr is shown in FIG. 3 where the effects of other tested conditions are averaged. 2 mM sodium propionate in the absence of increased NaCl resulted in a ~1.5 fold increase in the titer. Increased NaCl in the absence of sodium propionate resulted in a ~1.2 fold increase in the titer. Whereas 2 mM sodium propionate and increased NaCl in combination resulted in a ~2-fold higher yield than the baseline yield of the same process without the increase in NaCl and NaPr concentration following transfection. The observed ~2-fold increase is higher than what would be expected if the effect of NaPr and increased NaCl were additive.

Example 6. Effect of Sodium Chloride and/or Sodium Propionate on rAAV Yield

Figure 4:
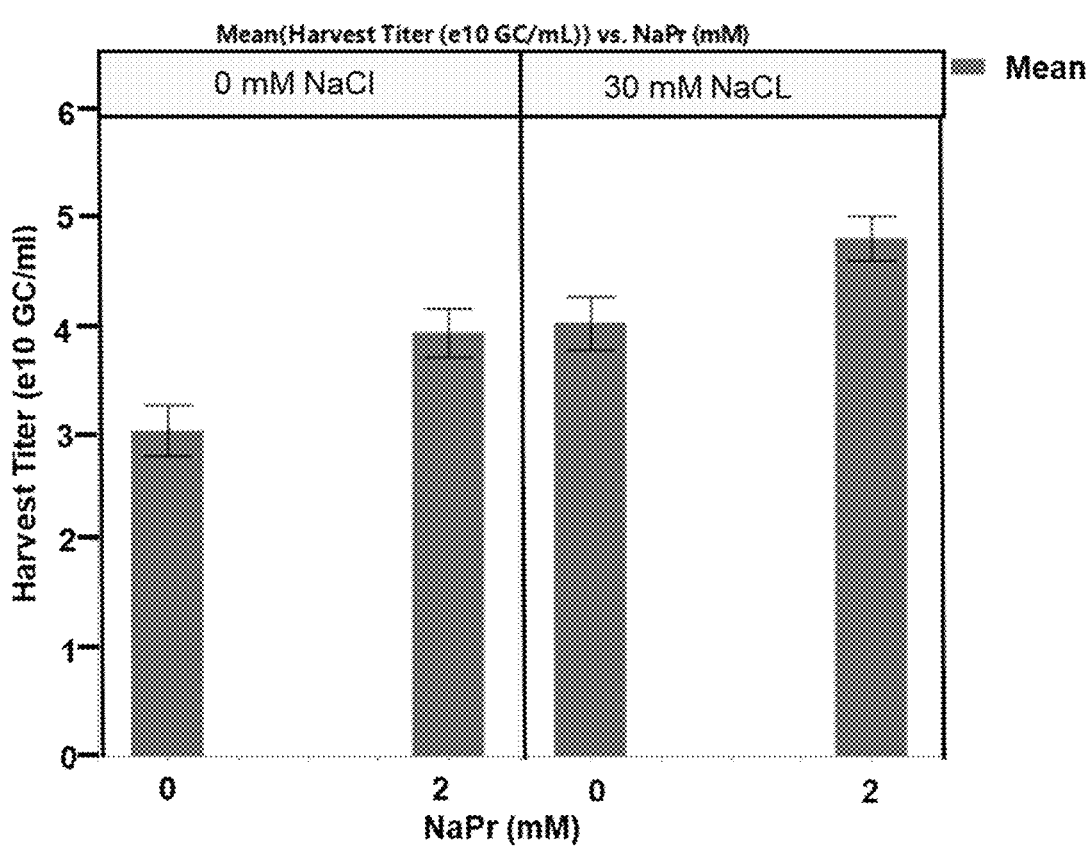
FIG. 4. rAAV9 yields obtained following the addition of sodium chloride, and/or sodium propionate.
Figure 5:
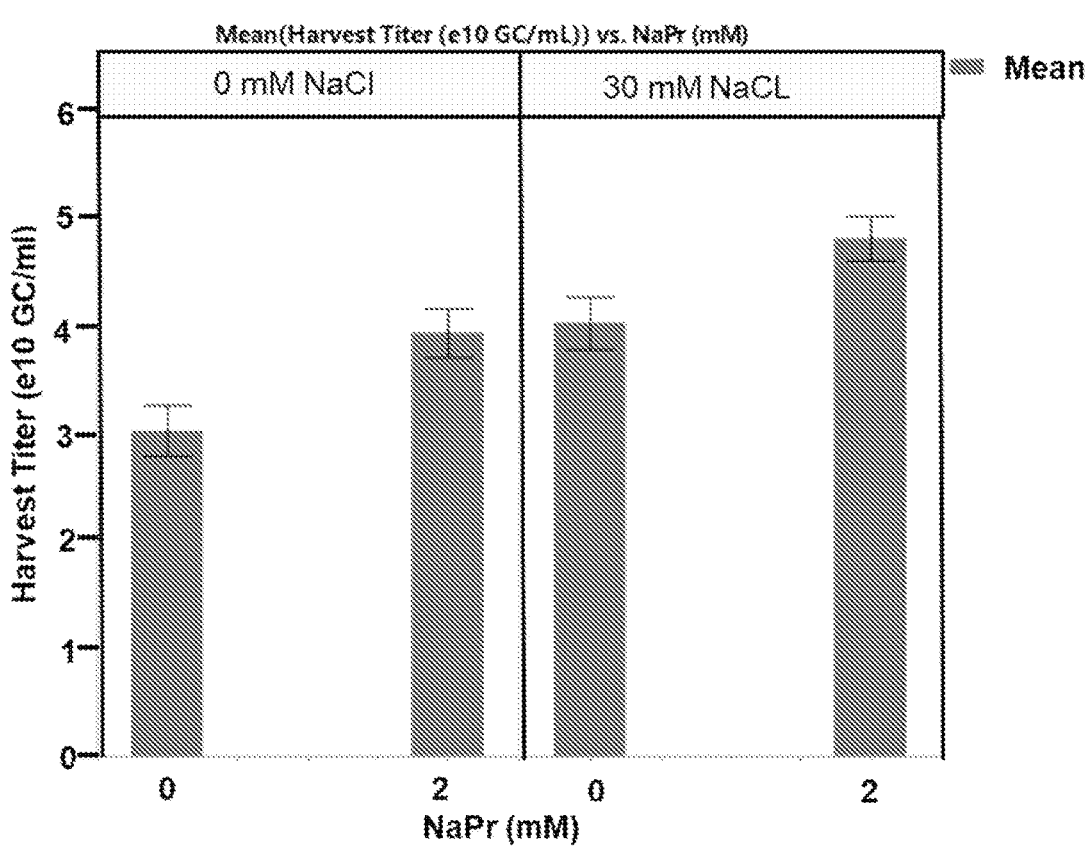

The effect of sodium chloride and sodium propionate (ThermoFisher Scientific) on rAAV yield in a suspension culture of HEK293 cells expressing rAAV9 particles encapsidating a transgene. HEK293 cells were seeded at 1×10e6 viable cell/ml density in advanced microscale bioreactors. The medium comprised 100 mM NaCl. At 48 hrs ECD (Elapsed Culture Duration), the cells were transfected with a mixture of polyethylenimine and 3 plasmids encoding adeno-virus helper functions, transgene and AAV 2/9 Rep/Cap. 20 hours after transfection, NaCl and sodium propionate (NaPr were added to the cultures. Conditions tested were 0 and 30 mM NaCl, 0 and 2 mM NaPr. Combinations of the conditions were tested in multiple reaction conditions using a Design of Experiment strategy. The supernatant of the cultures was harvested at 168 hours ECD, i.e., 5 days post-transfection. rAAV yields were obtained. A significant improvement in virus yield was obtained by adding both 30 mM of sodium chloride and 2 mM sodium propionate 20 hours post transfection. Resulting titer improvement by adding NaCl and/or NaPr is shown in FIG. 4 where the effects of other tested conditions are averaged. This is ~1.6-fold higher than the yield of the same process without the increase in NaCl and NaPr concentration following transfection.

While the disclosed methods have been described in connection with what is presently considered to be the most practical and preferred embodiments, it is to be understood that the methods encompassed by the disclosure are not to be limited to the disclosed embodiments, but on the contrary, is intended to cover various modifications and equivalent arrangements included within the spirit and scope of the appended claims.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What is claimed is:

1. A method for producing recombinant adeno associated virus (rAAV) particles, comprising
   a) providing a cell culture comprising a cell capable of producing rAAV and transfecting the cell with one or more polynucleotides comprising or encoding
      an rAAV genome to be packaged,
      adenovirus helper functions necessary for packaging,
      an AAV rep protein sufficient for packaging, and
      an AAV cap protein sufficient for packaging;
   b) adding to the cell culture sodium propionate to a final concentration between about 0.5 mM and about 3 mM;
   c) adding to the cell culture sodium chloride in sufficient amount to increase the final concentration of the sodium chloride by between about 20 mM and 50 mM; and
   d) maintaining the cell culture under conditions that allow packaging to produce the rAAV particles,
wherein the cell is transfected using a chemical based transfection method,
wherein the sodium propionate and the sodium chloride are added after transfecting the cell, and
wherein the sodium propionate and the sodium chloride are added no more than about 48 hours after transfecting the cell.

2. The method of claim 1, wherein prior to adding the sodium chloride, the cell culture comprises between about 90 mM and about 120 mM NaCl.

3. The method of claim 1, wherein the sodium chloride is added after adding the sodium propionate.

4. The method of claim 1, wherein the sodium chloride is added between about 5 minutes and about 6 hours after adding the sodium propionate.

5. The method of claim 1, wherein the sodium propionate is added between about 1 hour and about 48 hours after transfecting the cell.

6. The method of claim 1, wherein the cell is a HEK293 cell, HeLa cell, SF-9 cell, BHK cell, Vero cell, or PerC6 cell.

7. The method of claim 1, wherein the cell culture is a suspension culture.

8. The method of claim 1, further comprising recovering the rAAV particles.

9. The method of claim 1, wherein the cell culture produces between about 5×10e+10 genome copy (GC)/ml and about 1×10e+12 GC/ml rAAV particles.

10. The method of claim 1, wherein the cell culture produces at least about twice as many rAAV particles measured as GC/ml than a culture in sodium propionate chloride the absence of adding of the sodium propionate and the sodium chloride.

11. The method of claim 1, wherein the rAAV particles comprise a capsid protein of the AAV8, AAV9, AAV.rh10, AAV.rh20, AAV.rh39, AAV.Rh74, AAV.RHM4-1, or AAV.hu37 serotype.

12. The method of claim 1, wherein the rAAV genome comprises a transgene.

13. The method of claim 1, wherein the chemical based transfection method uses polyethylenimine (PEI).

14. The method of claim 1, wherein the sodium propionate and the sodium chloride are added separately in any order after transfecting the cell.

* * * * *